(12) United States Patent
Colvin et al.

(10) Patent No.: US 6,344,360 B1
(45) Date of Patent: Feb. 5, 2002

(54) DETECTION OF ANALYTES BY FLUORESCENT LANTHANIDE METAL CHELATE COMPLEXES CONTAINING SUBSTITUTED LIGANDS

(75) Inventors: Arthur E. Colvin, Mt. Airy; George Y. Daniloff, North Potomac; Aristole G. Kalivretenos, Columbia, all of MD (US); David Parker, Durham (GB); Edwin E. Ullman, Atherton, CA (US); Alexandre V. Nikolaitchik, Baltimore, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

(21) Appl. No.: 09/265,979

(22) Filed: Mar. 11, 1999

Related U.S. Application Data

(63) Continuation-in-part of application No. 09/037,960, filed on Mar. 11, 1998, now abandoned.

(51) Int. Cl.[7] .......................... G01N 33/00; G01N 33/50
(52) U.S. Cl. ........................... 436/94; 436/73; 436/79; 436/86; 436/87; 436/93; 436/95; 436/166; 436/172; 548/110; 534/15
(58) Field of Search .................... 436/73, 79, 86, 436/87, 91–99, 103, 106, 127–132, 166, 172, 518, 523, 524, 528, 531; 548/110; 534/15

(56) References Cited

U.S. PATENT DOCUMENTS

| | | | |
|---|---|---|---|
| 4,587,223 A | | 5/1986 | Soini et al. .................. 436/536 |
| 4,637,988 A | * | 1/1987 | Hinshaw et al. ............. 436/546 |
| 5,503,770 A | * | 4/1996 | James et al. ............ 252/301.16 |
| 5,512,246 A | * | 4/1996 | Russell et al. ................. 422/57 |
| 5,631,364 A | * | 5/1997 | Sundgrehagen et al. .... 540/128 |
| 6,001,573 A | * | 12/1999 | Roelant .......................... 435/6 |

FOREIGN PATENT DOCUMENTS

| | | |
|---|---|---|
| EP | 0561653 | 9/1993 |
| JP | 9-169772 | * 6/1997 |
| WO | 8707955 | 12/1987 |
| WO | 97/19188 | * 5/1997 |

OTHER PUBLICATIONS

L. A. Martarano et al, J. Phys. Chem. 1976, 80, 2389–2393, Oct. 1976.*
C. S.–H. Leung et al, Biochem. Biophys. Res. Commun. 1977, 75, 149–155, Jan. 1977.*
E. Lopez et al, Clin. Chem. 1993, 39, 196–201, Feb. 1993.*
H. Murakami et al, J. Chem. Soc. Perkin Trans. 2 1994, 975–981, May 1994.*
A. Abusaleh et al, Photochem. Photobiol. 1984, 39, 763–769, Jun. 1994.*
H. Shinmori et al, Tetrahedron 1995, 51, 1893–1902, Feb. 1995.*

(List continued on next page.)

Primary Examiner—Arlen Soderquist
(74) Attorney, Agent, or Firm—Rothwell, Figg, Ernst & Manbeck

(57) ABSTRACT

Compositions and methods for determining the presence or concentration of an analyte in a sample by exposing the sample to an indicator molecule comprising a fluorescent lanthanide metal chelate complex. The presence or concentration of the analyte in the sample is determined by observing and/or measuring the change in intensity of fluorescence emitted by the lanthanide metal chelate complex upon binding of the analyte to one or more recognition elements in the complex. The fluorescent indicator molecules can be used in various types of fluorescent sensing devices and are useful in various fields, including energy, medicine and agriculture.

18 Claims, 11 Drawing Sheets

OTHER PUBLICATIONS

H. Matsumoto et al, Chem. Lett. 1996, 301–302, Apr. 1996.*
S. Aime et al, Biochem. Mol. Biol. Int. 1996, 39, 741–746, Jul. 1996.*
J.–E. S. Sohna et al, Tetrahedron Lett. 1997, 38, 1381–1384, Feb. 1997.*
I. Hemmila et al, J. Alloys Comp. 1997, 249, 158–162, Mar. 1997.*
M. Li et al, Bioconjugate Chem. 1997, 8, 127–132, Mar. 1997.*
A. P. de Silva et al, Chem. Commun. 1997, 1891–892.*
Derwent Publications Ltd., London, GB; AN 97–389410; XP002109923.
James, T.D. et al., Novel Saccharide–Photoinduced Electron Transfer Sensors Based on the Interaction of Boronic Acid and Amine. *J. Am. Chem. Soc.*, 1995, 117, 8982–8987.

Yoon, J. et al., Fluorescent Chemosensors of Carbohydrates. A Means of Chemically Communicating the Binding of Polyols in Water Based on Chelation–Enhanced Quenching. *J. Am. Chem. Soc.*, 1992, 114, 5874–5875.

Parker, D. et al., "Luminescent Chemosensors for pH, Halide and Hydroxide Ions Based on Kinetically Stable, Macrocyclic Europium–Phenanthridinium Conjugates." *Chem. Commun.*, 1997, 1777–1778.

Huston, M.E. et al., "Chelation–Enhanced Fluorescence in 9, 10–Bis (TMEDA)anthracene." *J. Am. Chem. Soc.*, 1988, 110, 4460–4462.

* cited by examiner

DETECTION OF ANALYTES BY FLUORESCENT LANTHANIDE METAL CHELATE COMPLEXES CONTAINING SUBSTITUTED LIGANDS

CROSS-REFERENCE TO RELATED APPLICATIONS

This application is a continuation-in-part of application Ser. No. 09/037,960 filed Mar. 11, 1998 now abandoned.

STATEMENT REGARDING FEDERALLY SPONSORED RESEARCH OR DEVELOPMENT

Not applicable.

BACKGROUND OF THE INVENTION

1. Field of the Invention

This invention relates to fluorescent compounds useful as indicator molecules for detecting the presence or concentration of an analyte in a medium, such as a liquid, and to methods for achieving such detection. More particularly, the invention relates to fluorescent lanthanide metal chelate complexes containing substituted ligands and their use as indicator molecules for detecting the presence or concentration of an analyte such as glucose or other cis-diol compound in a medium, including a liquid medium such as a biological fluid.

2. Description of the Related Art

Certain rare-earth metal chelates emit visible light upon irradiation with UV light and different forms of visible light (e.g., violet or blue light), an emission which is characterized by the chelated cation. Some lanthanide ions, such as those of europium ($Eu^{3+}$), samarium ($Sm^{3+}$), terbium ($Tb^{3+}$), and to a lesser extent dysprosium ($Dy^{3+}$) and neodymium ($Nd^{3+}$), exhibit typical fluorescence characterized by the ion, especially when chelated to suitable excitation energy mediating organic ligands. The fluorescent properties of these compounds—long Stokes' shift, narrow band-type emission lines, and unusually long fluorescence lifetimes—have made them attractive candidates for fluorescent immunoassays and time-resolved fluorometric techniques.

The major emission lines of these fluorescent lanthanide chelates are formed from a transition called hypersensitive transition and are around 613–615 nm with $Eu^{3+}$, 545 (and 490) nm with $Tb^{3+}$, 590 and 643 nm with $Sm^{3+}$, and 573 with $Dy^{3+}$. See Hemmila, *Application of Fluorescence in Immunoassays*, 140–42 (1991). See also *Spectroscopy in Inorganic Chemistry*, vol. 2, at 255–85 (Academic Press 1971). Radiation is typically absorbed by the chelates at a wavelength characteristic of the organic ligand and emitted as a line spectrum characteristic of the metal ion because of an intramolecular energy transfer from the ligand to the central metal ion. The organic ligand absorbs energy and is raised or excited from its singlet ground state, $S_0$, to any one of the vibrational multiplets of the first singlet excited state, $S_1$, where it rapidly loses its excess vibrational energy. At this point, there are two possibilities: relaxation by an $S_1 \rightarrow S_0$ transition (ligand fluorescence) or intersystem crossing to one of the triplet states, $T_1$. See E. P. Diamandis et al., *Analytical Chemistry* 62:(22):1149A (1990); see also *Spectroscopy in Inorganic Chemistry*, vol. 2, at 255–85 (Academic Press 1971).

Fluorescent europium chelates are known to exhibit large Stokes shifts (~290 nm) with no overlap between the excitation and emission spectra and very narrow (10-nm bandwidth) emission spectra at 615 nm. In addition, the long fluorescence lifetimes (measurable in microseconds instead of the nanosecond lifetimes measurable for conventional fluorophores) of the chelates help filter out noise and other interference having a low fluorescent lifetime. The long fluorescent lifetimes thus permit use of the chelates for microsecond time-resolved fluorescence measurements, which further reduce the observed background signals. Additional advantages of using europium chelates include that europium chelates are not quenched by oxygen.

Line emissions of two europium (Eu) chelates, Eu-dibenzoylmethide and Eu-benzoylacetonate, have made the chelates attractive candidates for use in lasers. See H. Samuelson, et al. (*J. Chem. Physics* 39(1): 110–12 (1963)) Samuelson, et al. studied the fluorescence and absorption of the above two europium chelates as solids and in solution. Samuelson, et al. compared the fluorescent lifetimes of the europium chelates under various conditions with the lifetimes of europium fluorescence in other compounds. Based on this comparison, Samuelson, et al. suggested that the variation in lifetimes between the two groups of europium compounds is a result of the ligand-Eu interaction in the europium chelates. Specifically, Samuelson et al. determined that various emission lines from Eu-dibenzoylmethide showed fluorescent lifetimes of 480 +/–50 µs, which were significantly greater than the fluorescent lifetimes in other europium compounds.

Crosby, et al., *J. Chem. Physics* 34:743 (1961) had previously studied the role of intramolecular energy transfer in sensitizing ion emission from rare-earth metal chelates, including europium dibenzoylmethide and europium benzoylacetonate chelates. Whan, et al., *J. Mol. Spectroscopy* 8: 315–27 (1962) reported that the emission from chelates of a group of lanthanide metal ions ($Eu^{3+}$, $Tb^{3+}$, $Dy^{3+}$ and $Sm^{3+}$) was dominated by bright spectral lines characteristic of the individual rare-earth metal ions. Whan, et al. found that both the benzoylacetonates and dibenzoylmethides of $Eu^{3+}$ and $Tb^{3+}$ are especially bright emitters and that the bright line emissions and low yields of phosphorescence from these chelates indicated that intramolecular energy transfer from the ligands to the $Eu^{3+}$ and $Tb^{3+}$ ions of these chelates occurs efficiently. Whan, et al., at 324.

N. Filipescu, et al., *J. Physical Chem.* 68(11):3324 (1964) reported that the fluorescence spectra of europium and terbium β-diketone chelates are modified when substituents are changed in the organic ligand portion of the chelates. Filipescu, et al. discussed the relative intensity, spectral distribution, shifting, and splitting of the fluorescence lines of the europium and terbium chelates in relation to the nature of substituents, their position, molecular configuration, and the overall intramolecular energy transfer. Filipescu, et al. found that the overall fluorescence intensity characteristic of the ion depended on two factors: 1) the amount of energy available at the organic triplet, and 2) the efficiency of energy transfer to the ion.

Filipescu, et al. also found that the above two factors varied for different substituents. For instance, the substitution of europium dibenzoylmethide chelates with electron-donor methoxy groups in the meta position on the chelate was found to enhance the fluorescent emission of the europium ion, whereas paramethoxy substitution was found to decrease the europium fluorescence. Additionally, the effect was more pronounced for the di- than for the monomethoxy-substituted dibenzoylmethides. In contrast, an opposite effect was observed for nitro-substituted dibenzoylmethides of europium. The electron-withdrawing nitro groups attached to the para or meta positions were found to decrease the total ionic emission of europium. Additionally, the effect was more pronounced for di- than for monosubstituted dibenzoylmethides.

Filipescu, et al. further found that the strong ionic fluorescence emitted by europium para-phenyldibenzoylmethide indicated that increasing the size of the aromatic system enhanced the amount of energy transferred to the europium ion. This fact was confirmed by the emission results obtained for napthyl-substituted diketones which were found to have substantially higher ionic emissions than the dibenzoylmethide chelates. Filipescu, et al., at 3328–29.

E. Diamandis, et al., *Analytical Chemistry* 62(22): 1149A (1990), described how europium chelates can be used as labels in fluorescence immunoassays and DNA hybridization assays. With respect to fluorescent immunoasays, the authors described that europium chelates can be used as immunological labels in various assay configurations, including either competitive or noncompetitive assays.

U.S. Pat. No. 4,374,120 (Soini, et al.) describes a method for detecting a substance using a fluorescent lanthanide chelate complex as a marker. U.S. Pat. No. 4,374,120 also describes the use of β-diketones as enhancing ligands for promoting the strong fluorescence properties of certain lanthanide chelates, especially chelates of europium and terbium.

Wallac (Turku, Finland) developed a lanthanide metal chelate to replace radiation tags for conducting immunoassays, having the structure:

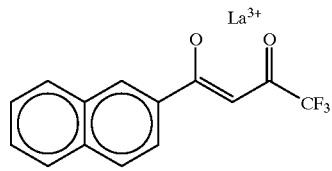

The Wallac molecule was found to behave very efficiently in dilute solutions. See Hemmila, *Applications of Fluorescence in Immunoassays*, p. 149 (1991).

Certain conditions are required for using lanthanide metal chelates in aqueous solutions, such as in biological fluids. For example, it is known that chelates must, first, be dissolved in the aqueous solution, and second, avoid being quenched by water molecules which tend to fill up the empty coordination sites of the lanthanide ion. However, various adducts or Lewis bases, such as phosphines, phosphine oxides, or nitrogen heterocycles, have been used in addition to the ligand structure to form an "insulating sheet" around the lanthanide ion, enhancing the fluorescence by preventing water molecules from penetrating into the complex's inner sphere. For example, solutions developed for fluorometric determinations of lanthanides in aqueous systems (e.g., immunoassays) have comprised β-diketones and trioctylphosphine oxide ("TOPO") as an adduct forming synergistic agent, and a detergent (e.g., Triton X100) which forms micelles and helps to solubilize the coordinated complex. See *Applications of Fluorescence in Immunoassays*, at 146–47.

Lanthanide metal chelate complexes have not been previously examined or constructed for the purpose of active detection of an analyte by utilizing a discrete and specific recognition element feature, such as a boronate group for detecting glucose and other cis-diols, through one or more ligands contained in the chelate complex. As discussed above, lanthanide metal chelates have been investigated primarily for use as laser dyes, substitute labels for radioisotopes, and for attachment to antibodies as labels in immunoassays. Lanthanide metal chelates also have been used for qualitative analytical procedures for detecting tetracycline.

Glucose is an organic compound indispensable to living organisms and plays an important role in information transmission, energy metabolism and structure formation in such organisms. For example, glucose, and more particularly, D-glucose, is crucial as an energy source for a variety of cells in constructing various organs. Glucose is stored in the liver as glycogen, which is released in body fluids as needed for energy consumption. The production and consumption of glucose are well balanced in the body fluids of a normal or healthy human being, maintaining the glucose concentration constant in the fluids. Thus, detecting sub-levels or supra-levels of glucose in the blood or the urine provides valuable information for diagnosing such diseases as diabetes and adrenal insufficiency.

A glucose sensor using an enzyme (e.g., as made by Yellow Springs Instruments (YSI), Ohio) is the best known practical measure for detecting glucose. This technique involves decomposing glucose with an enzyme (glucose oxidase) and measuring the amount of hydrogen peroxide produced by the decomposition through an appropriate means (such as by an electrode). Although this method is well established, the quality of the enzyme, which originates from a living body, will irreversibly change over time and cannot be recycled for reuse. Additionally, because the glucose is actually consumed in the detection reaction, the intrinsic ability of the glucose sensor to measure low levels of analyte is therefore limited.

It is well known that boronic acid-containing compounds bind to glucose. The mechanism is believed to occur through bonding of adjacent hydroxyl groups on glucose to hydroxyl groups on a boronate moiety, as drawn below:

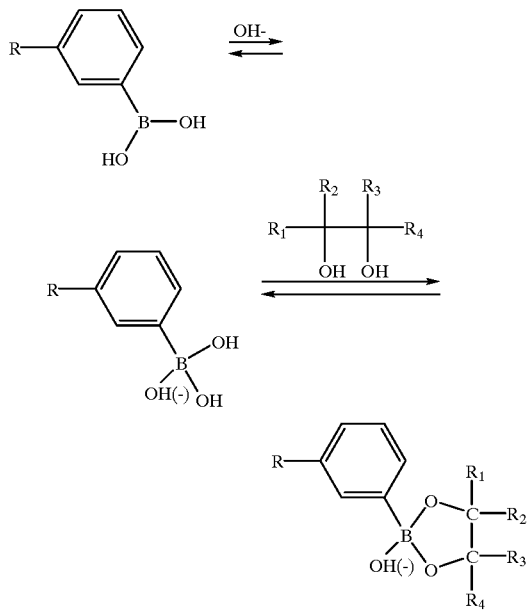

The complexation of carbohydrates, including glucose, with phenylboronic acid has been known for a long time and the reversibility of that interaction has served as a basis for the chromatographic separation of sugars. Specifically, in 1959, Lorand and Edwards reported association constants for aqueous associations of phenylboronic acid with many saturated polyols; binding interactions ranged from very weak (e.g., ethylene glycol, $K_d=360$ mM) to moderately strong (e.g., glucose, $K_d=9.1$ mM). See J. Yoon, et al., *Bioorganic and Medicinal Chemistry* 1(4): 267–71 (1993).

U.S. Pat. No. 5,503,770 (James, et al.) describes a fluorescent boronic acid-containing compound that emits fluorescence of a high intensity upon binding to saccharides, including glucose. The fluorescent compound has a molecular structure comprising a fluorophore, at least one phenylboronic acid moiety and at least one amine-providing nitrogen atom where the nitrogen atom is disposed in the vicinity of the phenylboronic acid moiety so as to interact intermolecularly with the boronic acid. Such interaction thereby causes the compound to emit fluorescence upon saccharide binding. U.S. Pat. No. 5,503,770 describes the compound as suitable for detecting saccharides. See also T. James, et al., *J. Am. Chem. Soc.* 117(35): 8982–87 (1995).

Additionally, fluorescent sensors using an anthrylboronic acid-containing compound for detecting blood glucose are known in the art. For example, J. Yoon, et al., *J. Am. Chem. Soc.* 114:5874–5875 (1992) describe that anthrylboronic acid can be used as a fluorescent chemosensor for signaling carbohydrate binding, including binding of glucose and fructose.

An object of the present invention is to detect the presence or concentration of an analyte in a medium such as a liquid or gas by measuring any change in fluorescence emitted by a lanthanide metal chelate complex upon binding of the analyte to one or more chelators of the chelate complex through an analyte-specific recognition element.

Another object of the present invention is to provide an analyte-specific, recognition element-containing lanthanide metal chelate complex as an indicator molecule for detecting the presence or concentration of an analyte such as glucose or other cis-diol compound in a medium such as a liquid.

BRIEF SUMMARY OF THE INVENTION

The present invention is directed to an indicator molecule for detecting the presence or concentration of an analyte, comprising a fluorescent lanthanide metal chelate complex having the formula:

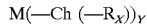

wherein:
M represents a lanthanide metal ion; Ch represents a chelator comprising a ligand, preferably an organic ligand which can comprise any one or more of a β-diketone or a nitrogen analog thereof, a dihydroxy, a carboxyl coordinating heterocycle, an enol, a macrobicyclic cryptand (i.e., a cage-type ligand), a phenylphosphonic acid, or a polyaminopolycarboxylic acid. The organic ligand of Ch can also comprise any one or more of a heterocycle of nitrogen, sulfur, and linked carboxyls. The organic ligand of Ch can further comprise any one or more of an alkane or alkene group, preferably containing 1 to 10 carbon atoms, as well as aromatic, carbocyclic or heterocyclic moieties, including benzyl, napthyl, anthryl, phenanthryl, or tetracyl groups. Furthermore, one or more chelators complexed with M can be the same or a mixture of different chelators (so-called "mixed ligand or ternary chelates").

R represents an analyte-specific recognition element, one or more of which is bound to one or more ligands of the chelate complex, but need not be linked to every ligand of the chelate complex. In a preferred embodiment of the present invention, R can be a boronate group or a compound containing a boronate group for detecting glucose or other cis-diol compound.

X represents the number of recognition elements R bound to each of one or more chelators. X can be an integer from 0 to 8, and in certain preferred embodiments of the invention, X=0 to 4 or X=0 to 2. Additionally, the number of recognition elements R bound to each of one or more chelators may be the same or different, provided that for one or more chelators, X>0. Y represents the number of chelators complexed with M, and can be an integer from 1 to 4. In certain preferred embodiments of the invention, Y=1, Y=3 or Y=4.

The present invention also is directed to a fluorescent lanthanide metal chelate complex, as defined above.

The present invention further is directed to methods for detecting the presence or concentration of an analyte by utilizing the above indicator molecule and fluorescent lanthanide metal chelate complex. The method comprises the steps of exposing the sample to an indicator molecule comprising a fluorescent lanthanide metal chelate complex having the above-defined formula, and measuring any change in fluorescence emitted by the lanthanide metal chelate complex, and therey detecting the presence or concentration of the analyte.

In the present invention, the presence or concentration of the analyte is detected by measuring any change in fluorescence emitted by the lanthanide metal chelate complex upon binding of the analyte to one or more chelators of the chelate complex through one or more analyte-specific recognition elements. Specifically, the presence or concentration of an analyte, such as glucose or other cis-diol compound, is determined by observing and/or measuring the change in intensity or lifetime of fluorescence emitted by the fluorescent metal ion (i.e., the fluorescence is attenuated, enhanced or shifted in wavelength) upon binding of the analyte to the analyte-specific recognition element of the chelate, which for detecting glucose or other cis-diol compound is a boronate-containing recognition element.

The present invention offers the advantage of being able to detect an analyte, such as glucose or other cis-diol compound, in an analyte-specific manner in a medium such as a liquid or a gas, utilizing a fluorescent indicator molecule having a fluorescent lifetime of sufficient length (measurable in microseconds instead of nanoseconds), as well as having a long Stoke's shift, thereby decreasing the effect of any background noise and other interference which would reduce the sensitivity of the analyte detection, and is not concentration quenched.

BRIEF DESCRIPTION OF THE DRAWINGS

Preferred embodiments of the indicator molecule of the invention will be illustrated by reference to the accompanying drawings in which.

DETAILED DESCRIPTION OF THE INVENTION

Figure 1:
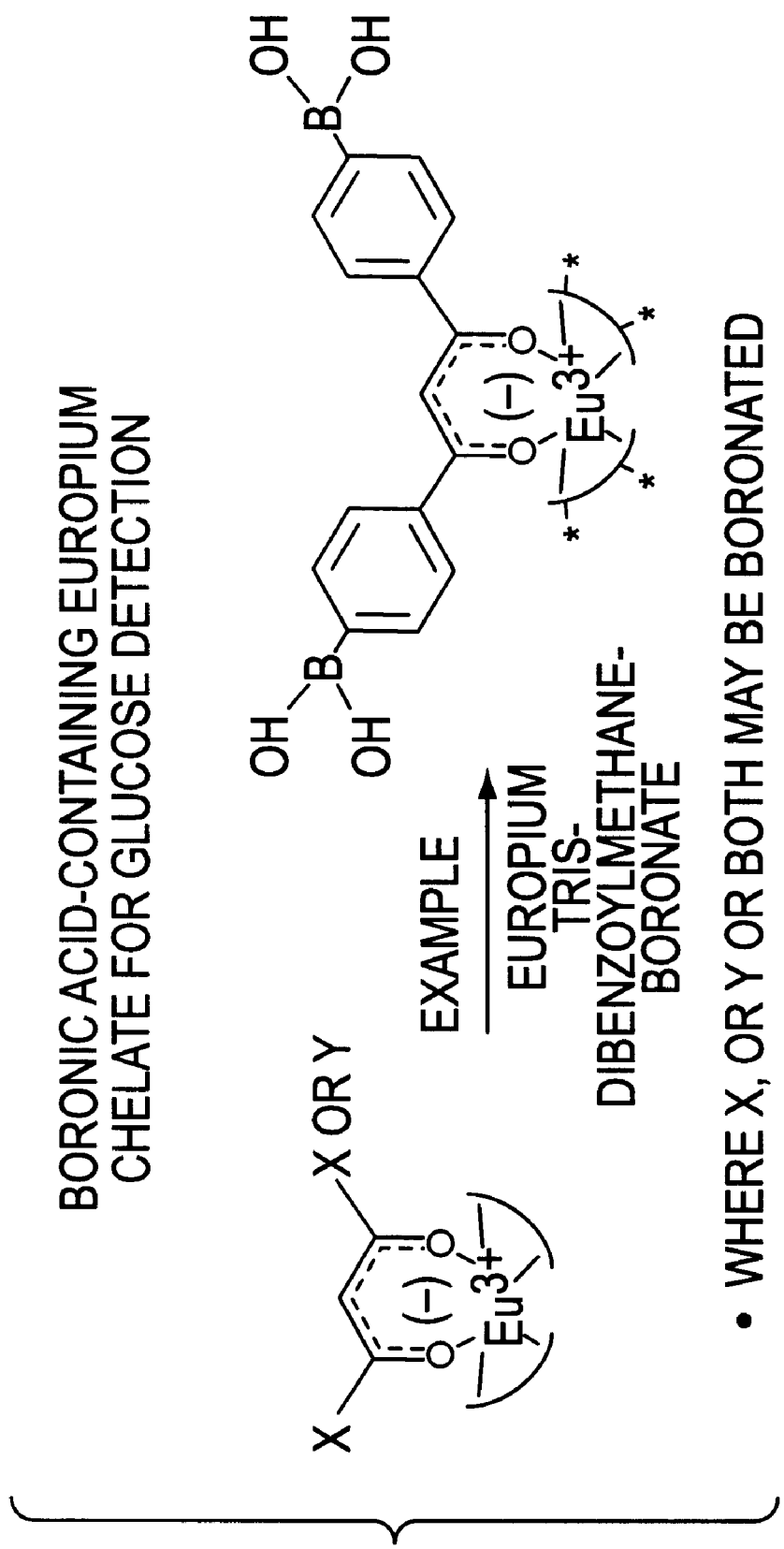
FIG. 1 illustrates a boronic acid-containing europium chelate in accordance with the present invention (shown having only one ligand for purposes of clarity).
Figure 2:
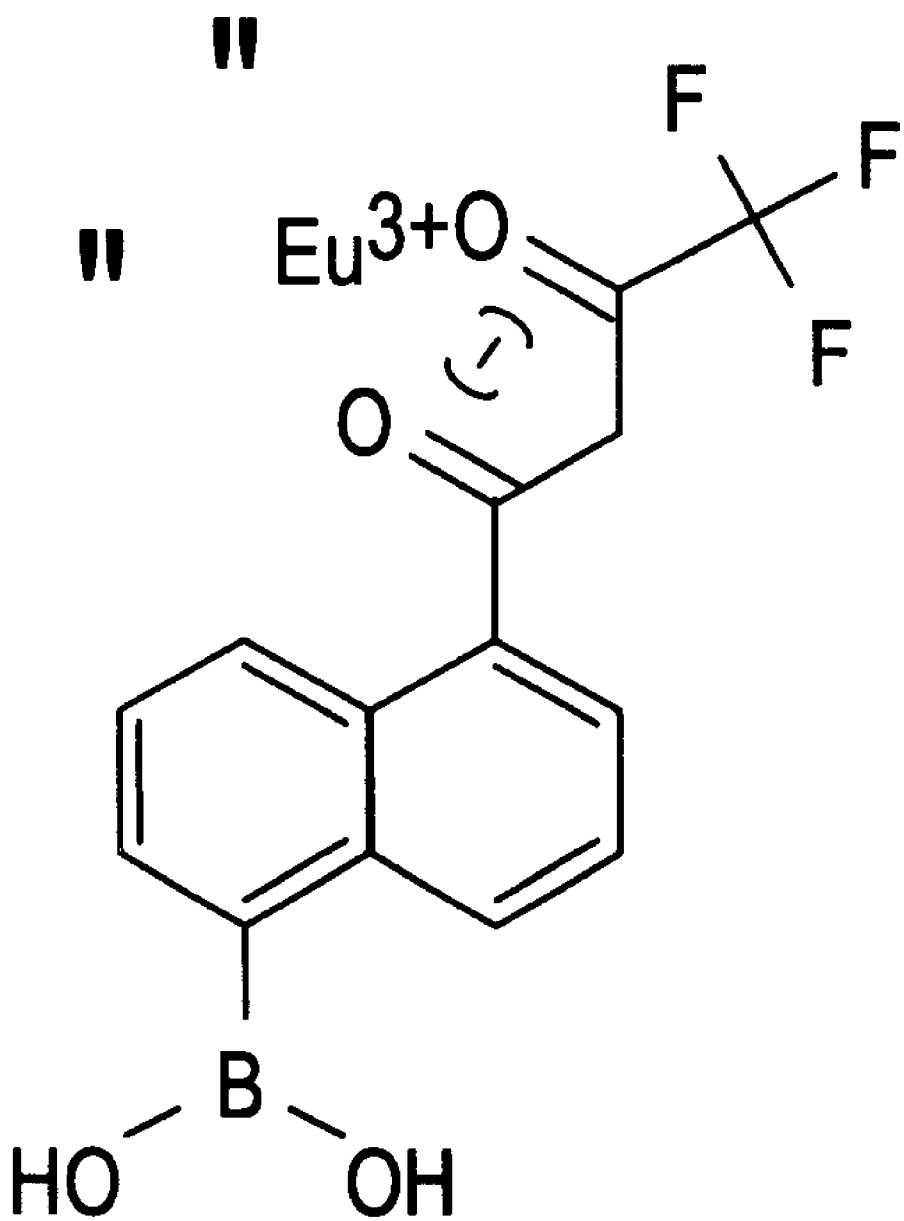
FIG. 2 also illustrates a boronic acid-containing europium chelate in accordance with the present invention.

As stated above, the presence or concentration of an analyte is determined in the present invention by observing and/or measuring the change in intensity or lifetime of fluorescence emitted by the fluorescent indicator molecule after binding to an analyte through one or more analyte-specific recognition elements in the indicator molecule. The fluorescent indicator molecule comprises a lanthanide metal chelate complex having the formula:

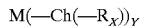

wherein:

M represents a lanthanide metal ion; Ch represents a chelator comprising a ligand, preferably an organic ligand, which can comprise any one or more of a β-diketone or a nitrogen analog thereof, a dihydroxy, a carboxyl coordinating heterocycle, an enol, macro-bicyclic cryptand (i.e., a cage-type ligand), a phenylphosphonic acid, a cyclen (tetra aliphatic carboxylates or phosphonates of 1,4,7,10-tetraazacyclododecane) or a polyamino-polycarboxylic acid. The organic ligand of Ch can also comprise any one or more of a heterocycle of nitrogen, sulfur, and linked carboxyls.

R represents an analyte-specific recognition element, one or more of which is bound to one or more ligands of the chelate complex, but need not be linked to every ligand of the chelate complex. In a preferred embodiment of the present invention, R can be a group for detecting glucose or other cis-diol or cis-diol acting compounds. Such groups include boronates, arsenites and germanates, and compounds containing those groups. Representative boronate-containing compounds include those having the following general structures (in each structure, R' and R" are each independently fused aryl; aliphatic; primary, secondary or tertiary amine; amide; carboxyl; ketone; ester; alcohol; or aldehyde; and Y and Z are each independently aliphatic, alkoxy or aryl):

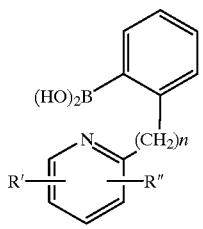

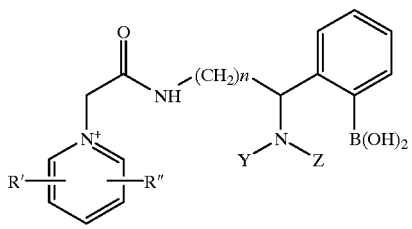

wherein n is 0 or 1 in the left structure and 0, 1 or 2 in the right structure;

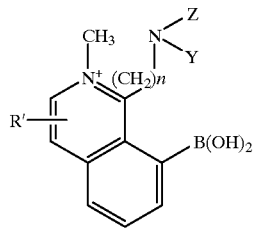

wherein n is 1;

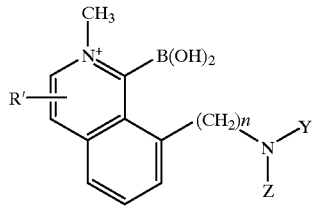

wherein n is 0 or 1;

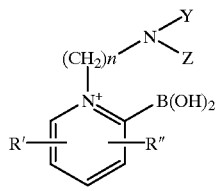

wherein n is 2;

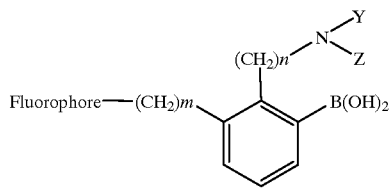

wherein m is 0–5 and n is 1 or 2; and

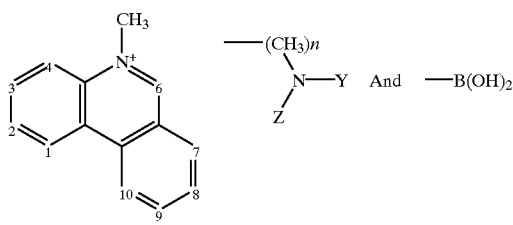

wherein n is 0 or 1, and the boronic acid and amine substituents are located as a pair on positions 1 and 10, 3 and 4, 6 and 7, 7 and 8 or 9 and 10.

Some specific boronate-containing compounds include:
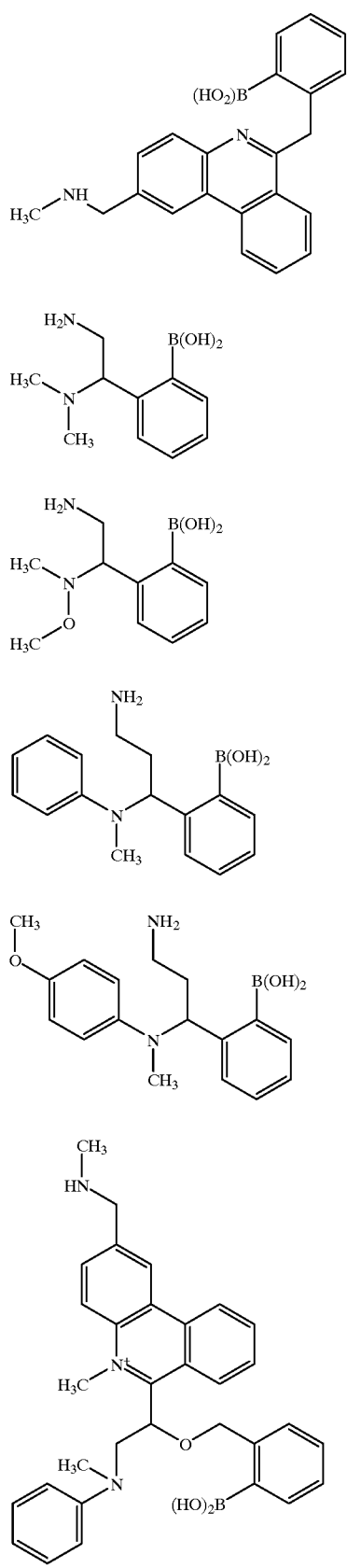
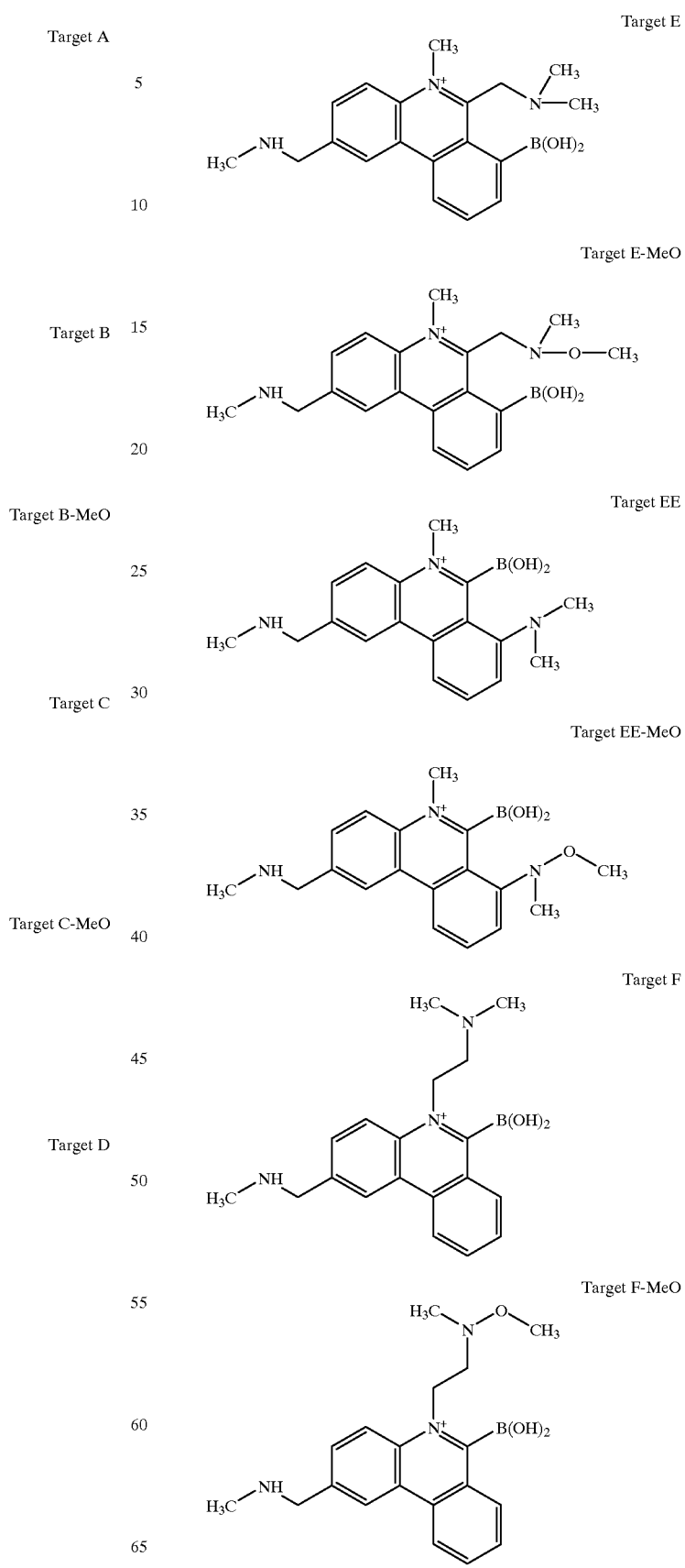

Target F-Phe
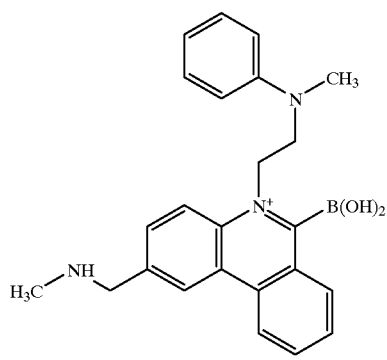
Target G
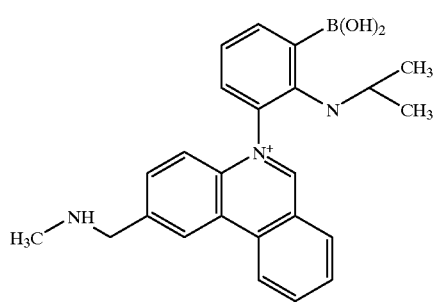
Target G-MeO
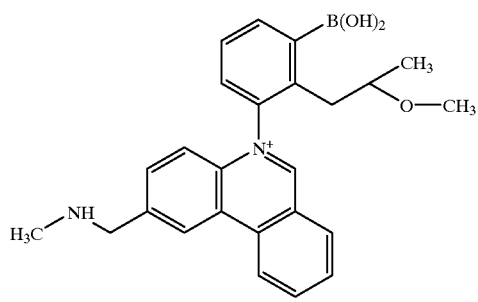
Target H
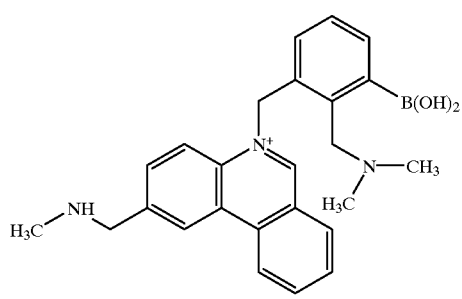
Target H-MeO
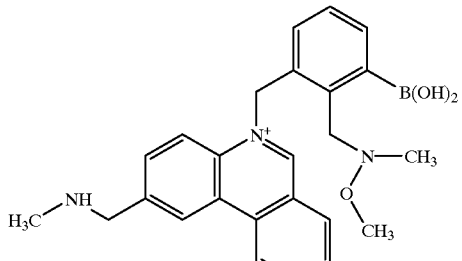
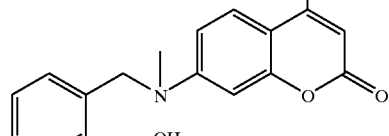
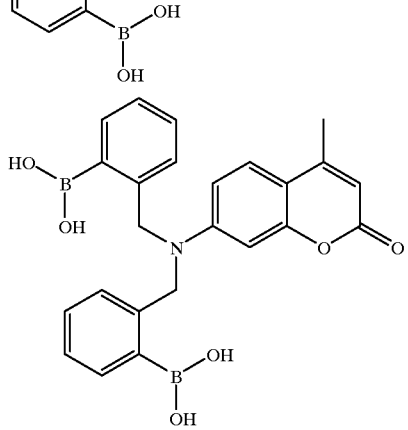
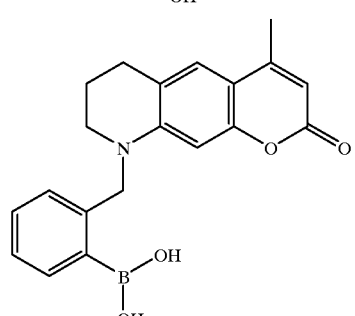
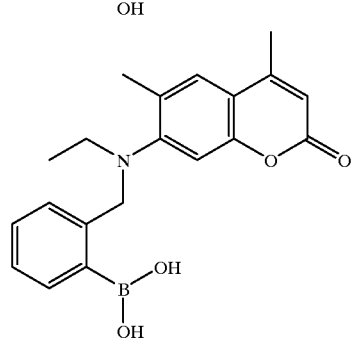
Examples of cis-diol analyte compounds other than glucose include other sugars such as fructose and glycerol. Catechols (o-dihydroxybenzenes) and catecholamines, including hormones such as dopamine, epinephrine and norepinephrine, contain adjacent (ortho) hydroxyls which mimic cis-diols with respect to their reactivity with boronate recognition elements.

The lanthanide metal ion M can be that of europium ($Eu^{3+}$), samarium ($Sm^{3+}$), terbium ($Tb^{3+}$), dysprosium ($Dy^{3+}$) or neodymium ($Nd^{3+}$), and is preferably an ion of europium ($Eu^{3+}$) or terbium ($Tb^{3+}$).

The ligand of the chelator Ch can also be an organic ligand comprising any one or more of an alkane or alkene group, preferably containing 1 to 10 carbon atoms, as well as aromatic, carbocyclic or heterocyclic moieties, including benzyl, napthyl, anthryl, phenanthryl or tetracyl groups. The ligand can also comprise groups such as —$CF_3$ and $C_2F_5$, as long as the ligand further comprises a moiety to which an analyte-specific recognition element R can be bound, if desired. Additionally, any ligand of a chelate complex may be inorganic instead of organic.

X represents the number of recognition elements R bound to each of one or more chelators. X can be an integer from 0 to 8, and in certain preferred embodiments of the invention, X=0 to 4 or X=0 to 2. Additionally, the number of recognition elements R bound to each of one or more chelators may be the same or different, provided that for one or more chelators, X>0. Y represents the number of chelators complexed with M, and can be an integer from 1 to 4. In certain preferred embodiments of the invention, Y=1, Y=3 or Y=4.

In certain embodiments of the present invention, the lanthanide metal chelate complex can comprise a mixture of different chelators wherein one or more of the chelators do not contain an analyte-specific recognition element R. The advantages of using such a mixed ligand chelate, also known as a ternary ligand chelate, include that some organic ligands, such as polyamino-polycarboxylic acids, are more soluble in water than other ligands, such as a β-diketone, such as a polyamino-polycarboxylic acid, which promote the water solubility of the chelate complex.

In other embodiments of the present invention, one or more chelators of the chelate complex can further comprise an —$NH_2$ or —OH group, or any other substituent by which the chelate complex can attach covalently to a linker or polymer such as a polylysine, or other solid support.

In order to achieve energy transfer from the light absorbing portion of the complex to the lanthanide metal ion, the triplet state energy of the light absorbing portion is preferably above about 230 kJ/mol. Preferred light absorbing portions include phenanthridine (258 kJ/mol), psoralen (262 kJ/mol), phenoxazine (261 kJ/mol), phenanthrene (258 kJ/mol), triphenylene (280 kJ/mol), benzophenone (287 kJ/mol), carbazole (293 kJ/mol) and coumarin (258 kJ/mol).

The fluorescence of the lanthanide metal chelate complex of the present invention is modulated in an analyte-specific manner by the binding of an analyte to one or more chelators of the chelate complex through one or more recognition elements R.

The fluorescent indicator molecules of the present invention can be used for detecting a variety of different possible chemical analytes which are reactive with, and thus can be detected in a specific manner by, an analyte-specific recognition element R. Preferred analytes for detection using the present invention are analytes such as glucose, fructose and other cis-diol compounds. However, depending on the choice of the recognition element, the indicator molecules of the present invention are also useful to detect many other analytes. For example, the following molecule has a recognition element which makes it useful as a pH indicator (see Lippitsch, et al., *Sensors and Actuators B* 38–39 (1997) 96–102):

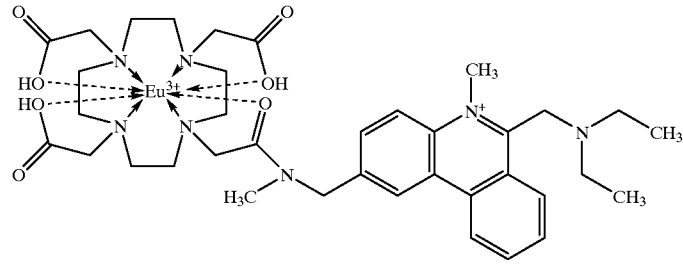

Therefore, in at least one embodiment of the invention, the lanthanide metal chelate complex can comprise, first, one or more β-diketones containing one or more analyte-specific recognition elements, and second, one or more other ligands In addition, following is one of many possible compounds which contains a recognition element which may be used to bind a zinc analyte (see, e.g., Huston, et al., *JACS* 1988, 110, 4460):

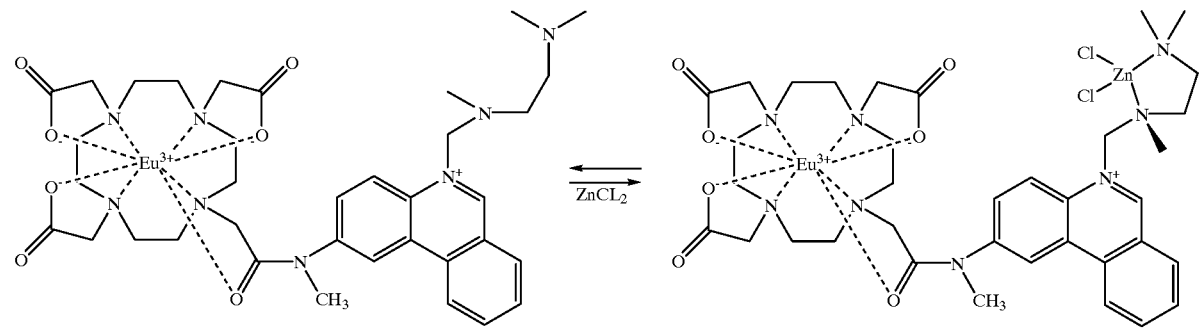

Zinc binding as shown will increase the fluorescence of that indicator molecule, and others like it containing a similar recognition element. Further, following is one of many possible compounds which contains a recognition element which may be used to detect a potassium analyte (see, e.g., Sousa, et al., *ACS Symposium Series* 538, 1992, pp. 10–24):

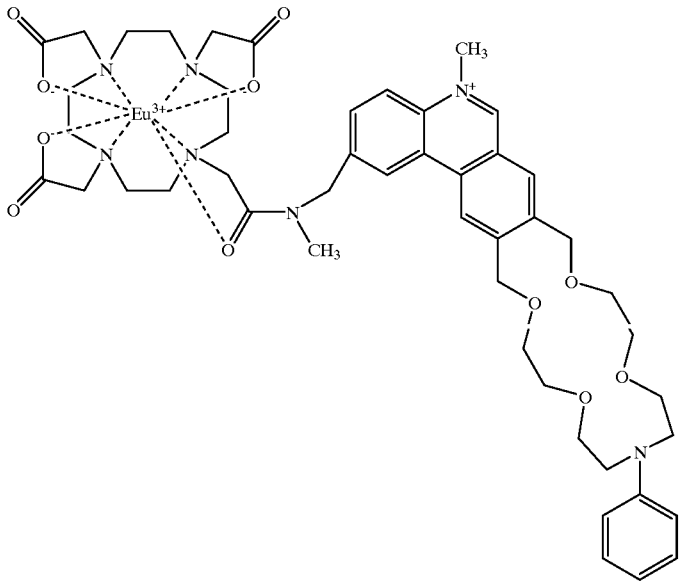

In that compound, the potassium ion is coordinated within the crown ether moiety, causing a three-dimensional configuration change such that the aniline portion of the molecule is folded over onto the phenanthridine portion, resulting in the quenching of fluorescence.

The chemical analytes detectable using the indicator molecules of the present invention can exist in various different solid, gaseous and liquid forms. Additionally, analytes can be detected using the indicator molecules of the present invention in various mediums, including both liquid and gaseous mediums.

A number of possible uses exist for the fluorescent compounds of the present invention, including uses as indicator molecules in the fields of energy, medicine and agriculture. For example, the fluorescent compounds can be used as indicator molecules for detecting sub-levels or supra-levels of glucose in blood or urine, thus providing valuable information for diagnosing such diseases as diabetes and adrenal insufficiency. Medical/pharmaceutical production of glucose for human therapeutic application requires monitoring and control. Possible uses for the present invention in agriculture include detecting levels of an analyte such as glucose in soybeans and other agricultural products. Glucose must be carefully monitored in critical harvest decisions for such high value products as wine grapes. As glucose is the most expensive carbon source and feedstock in fermentation processes, glucose monitoring for optimum reactor feed rate control is important in power alcohol production. Reactor mixing and control of glucose concentration also is critical to quality control during production of soft drinks and fermented beverages, for which production is consumed the largest amounts of glucose and fermentable (cis-diol) sugars internationally.

Various detection techniques also are known in the art that can make use of the fluorescent compounds of the present invention. For example, the fluorescent compounds of the invention can be used in fluorescent sensing devices (e.g., U.S. Pat. No. 5,517,313) or can be bound to polymeric material such as test paper for visual inspection. This latter technique would permit, for example, glucose measurement in a manner analogous to determining pH with a strip of litmus paper. The fluorescent molecules described herein may also be utilized as simple reagents with standard benchtop analytical instrumentation such as spectrofluorometers or clinical analyzers as made by Shimadzu, Hitachi, Jasco, Beckman and others. These molecules would also provide analyte specific chemical/optical signal transduction for fiber optic-based sensors and analytical fluorometers as made by Ocean Optics (Clearwater, Fla.), or Oriel Optics.

In a preferred embodiment of the present invention, various possible chelators, one or more of which can be complexed with a lanthanide metal ion, comprise an organic ligand having attached thereto one or more boronate groups as the analyte-specific recognition group R, examples of which are shown below.

A. β-Diketones

The chelator Ch of the lanthanide metal chelate complex of the present invention can be a β-diketone-based ligand, examples of which are provided below.

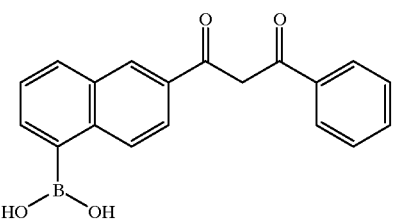

-continued
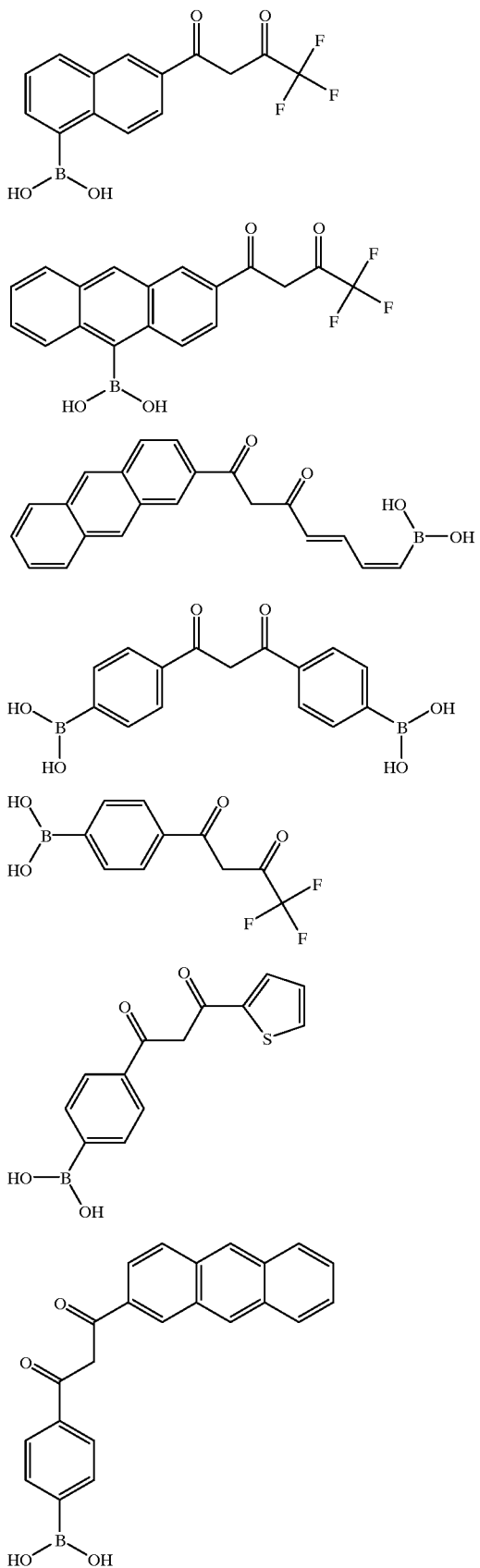
-continued
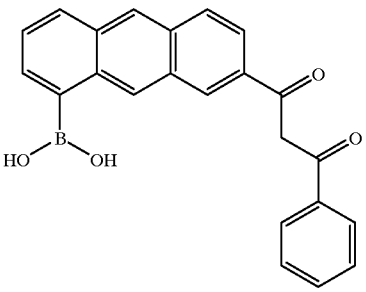
B. Macrobicyclic Cryptands (Cage-Type Ligands)
The chelator Ch in other embodiments of the present invention can be a macrobicyclic cryptand (or cage-type ligand), an example of which is shown below, having the form:
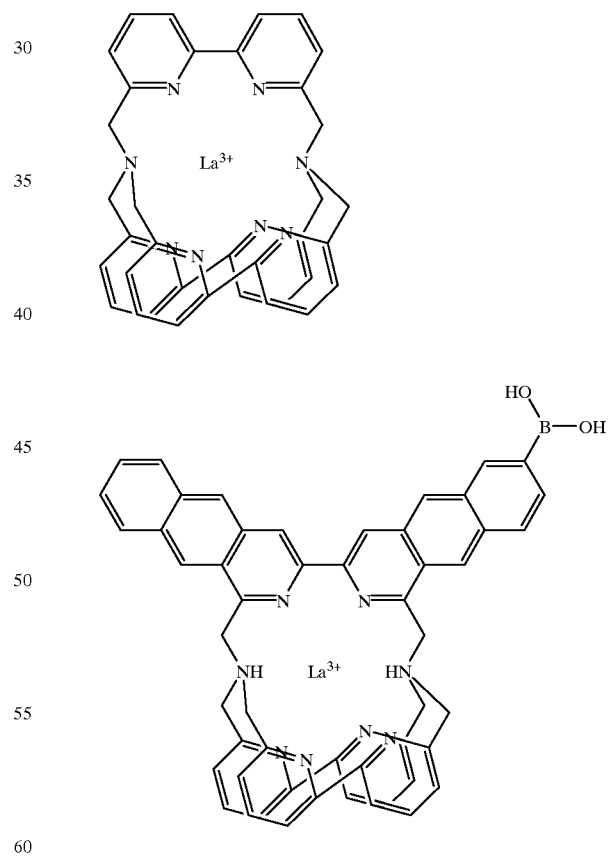
The chelator Ch in another embodiment of the present invention can be a macrobicyclic cryptand having the following structure.

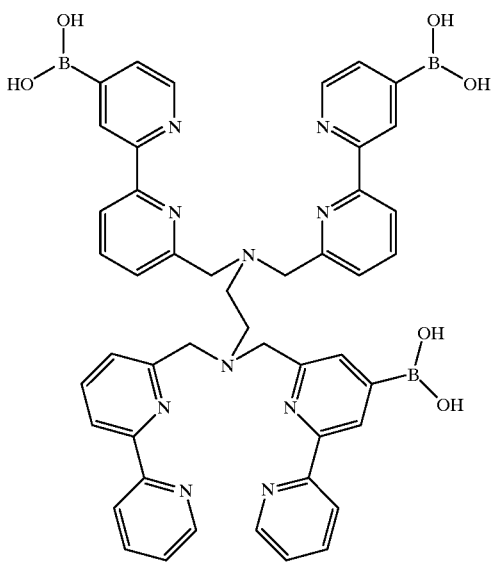

C. Nitrogen Heterocycles and Carboxylate Coordinate Ligands

Embodiments of the chelator Ch of the lanthanide metal chelate complexes of the present invention also include the following nitrogen heterocycles and carboxylate coordinate ligands.

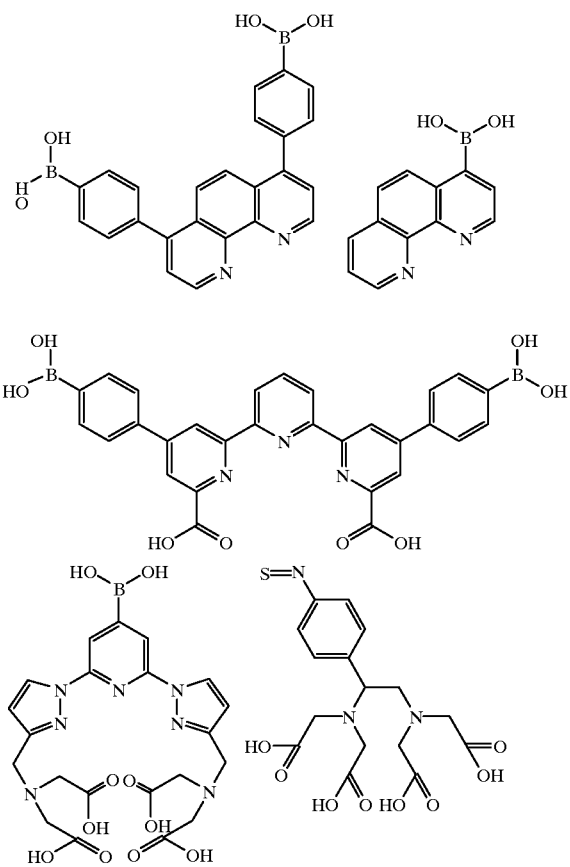

Some of the most preferred fluorescent, boronate recognition element-containing lanthanide chelates of the present invention include the following europium chelates (shown having only one ligand for purposes of clarity) comprising the following structures:

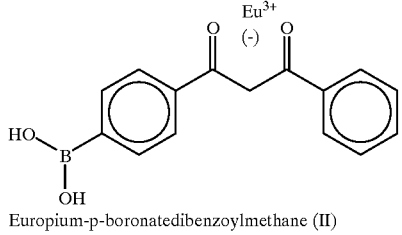

Europium-p-boronatedibenzoylmethane (II)

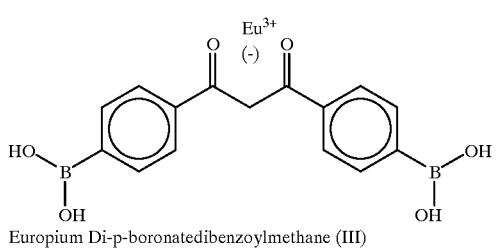

Europium Di-p-boronatedibenzoylmethane (III)

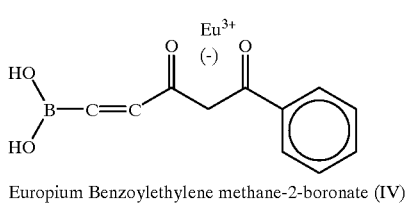

Europium Benzoylethylene methane-2-boronate (IV)

In a preferred embodiment of the present invention, a boronate-containing recognition element which is analyte-specific for glucose or other cis-diol compound was attached to a fluorescent europium (tetrakis) beta-naphthoyltrifluoroacetate (Eu-bNTA) chelate. The organic ligand portion of the chelate was known to form a shell around the lanthanide metal ion (e.g., europium), as drawn below:

Additionally, that different solvents affect the fluorescent decay time of the lanthanide metal ion (e.g., water quenches the fluorescence of the europium ion) also was known. It was thus investigated whether modifying the organic ligands of the outer shell with an analyte-specific recognition element (e.g., a boronate-containing recognition element) would perturb the decay time of the europium ion to any notable extent. The following europium chelate, europium (tetrakis) naphthoyltrifluoromethane (Eu-bNTA) boronate, was synthesized and tested.

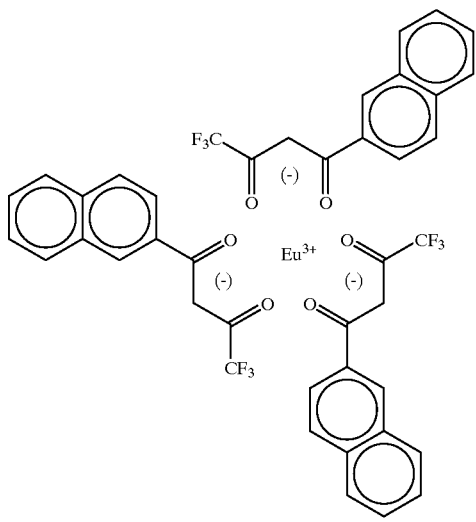

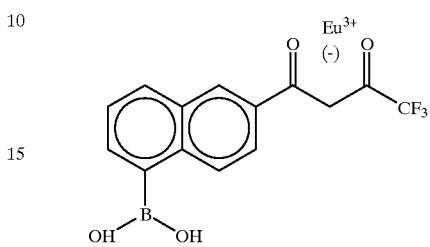

the fluorescence of the europium ion) also was known. It was thus investigated whether modifying the organic ligands of the outer shell with an analyte-specific recognition element (e.g., a boronate-containing recognition element) would perturb the decay time of the europium ion to any notable extent. The following europium chelate, europium (tetrakis) naphthoyltrifluoromethane (Eu-bNTA) boronate, was synthesized and tested.

Additionally, that different solvents affect the fluorescent decay time of the lanthanide metal ion (e.g., water quenches Eu-bNTA boronate was found to have an excitation wavelength of about 340 nm and an emission wavelength which was the same as for other europium chelates, about 613 nm.

Other preferred compounds for the detection of cis-diols including glucose include the following.

Target A

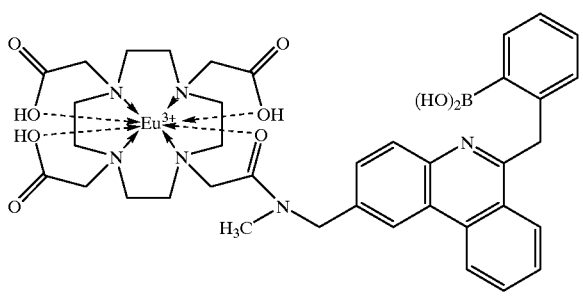

Target B-1

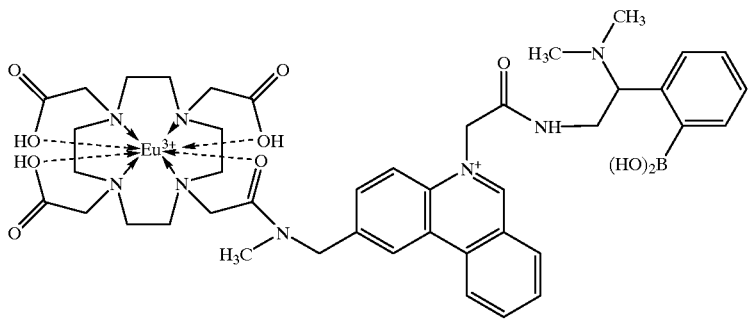

Target B-2

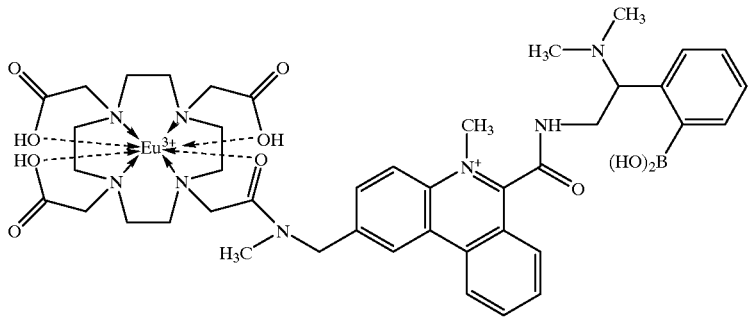

-continued
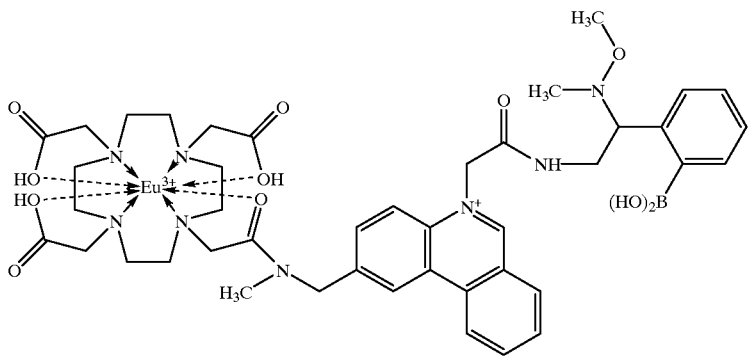
Target B-MeO-1
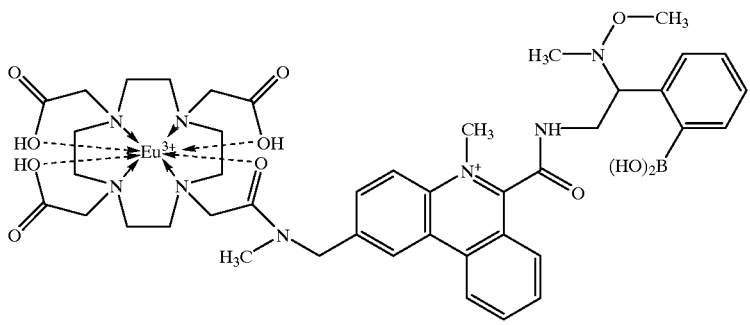
Target B-MeO-2
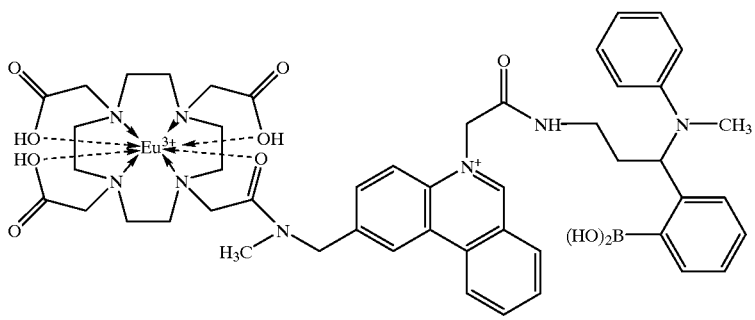
Target C-1
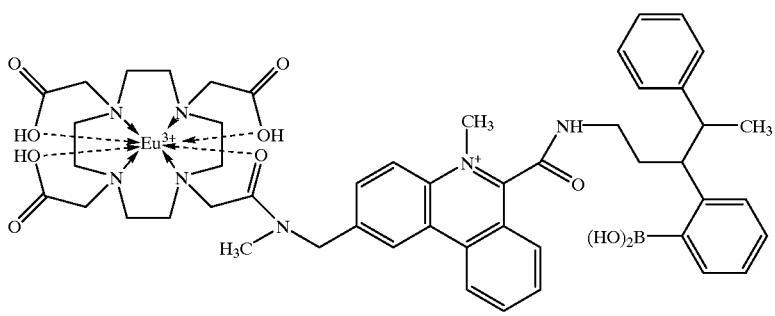
Target C-2

-continued
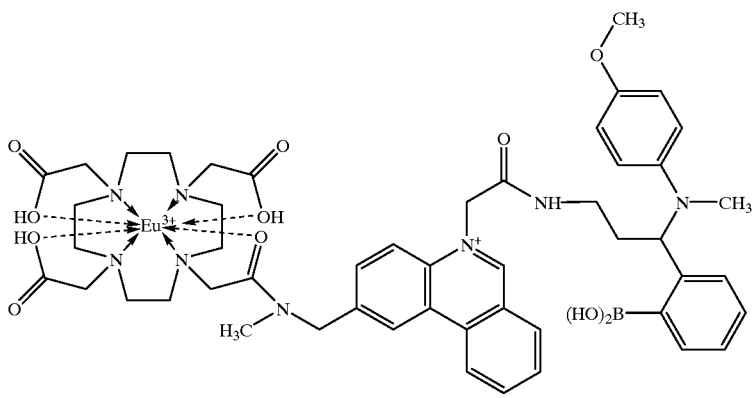
Target C-MeO-1
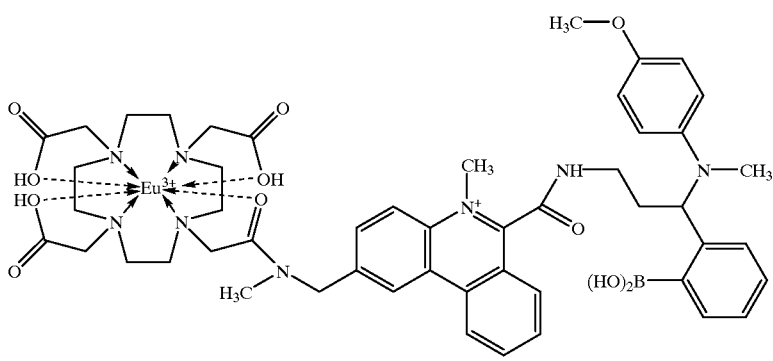
Target C-MeO-2
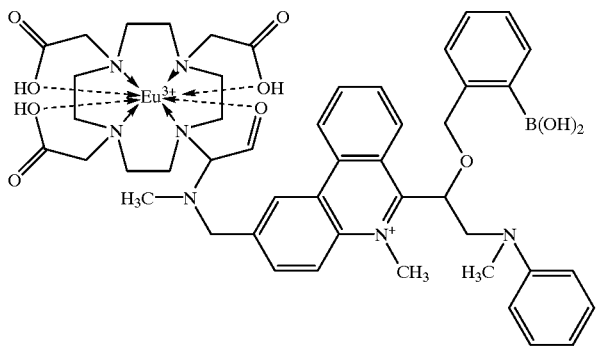
Target D
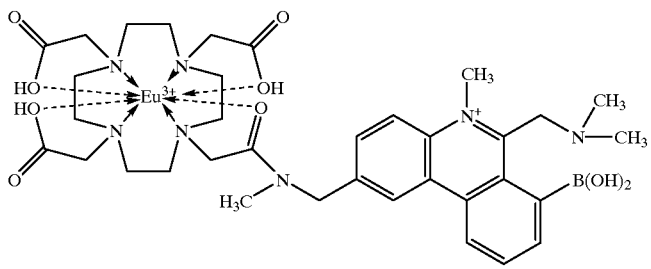
Target E -continued
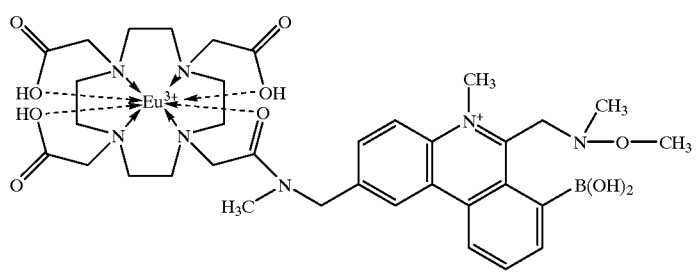
Target E-MeO
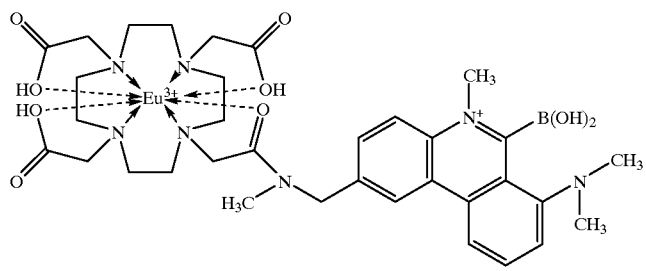
Target EE
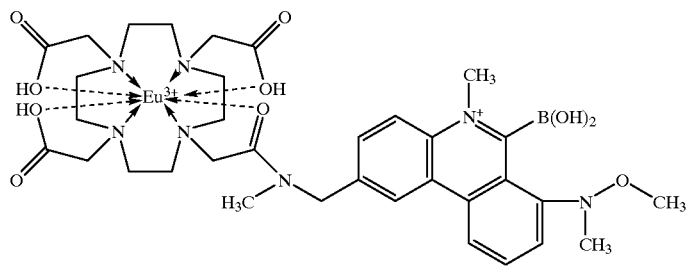
Target EE-MeO
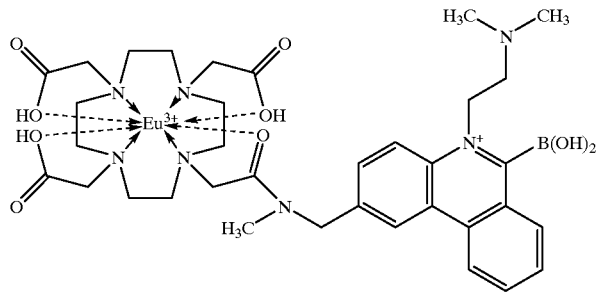
Target F
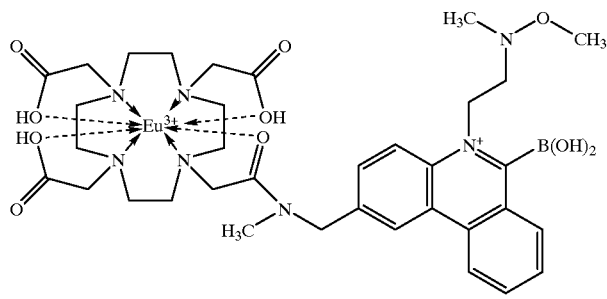
Target F-MeO -continued
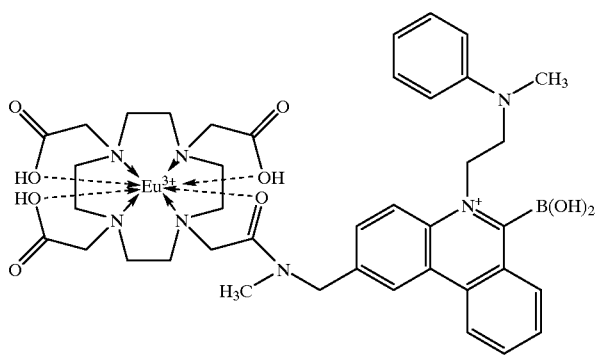
Target F-Phe
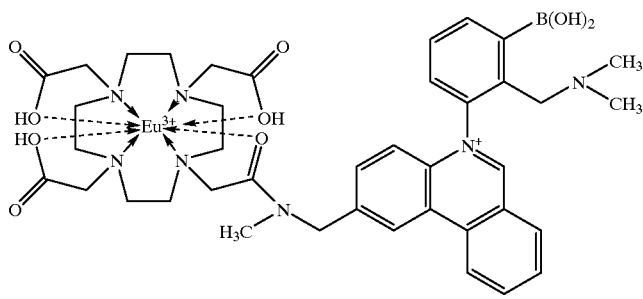
Target G
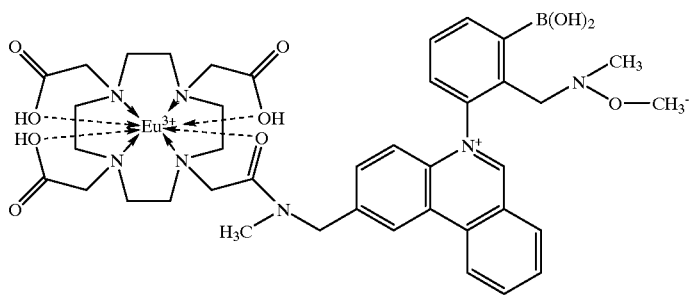
Target G-MeO
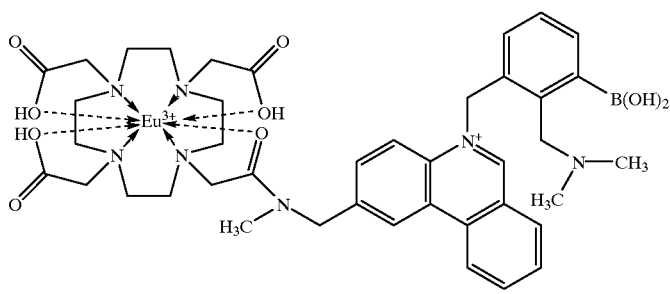
Target H
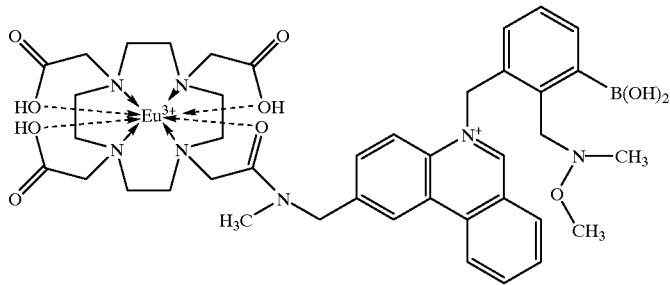
Target H-MeO -continued

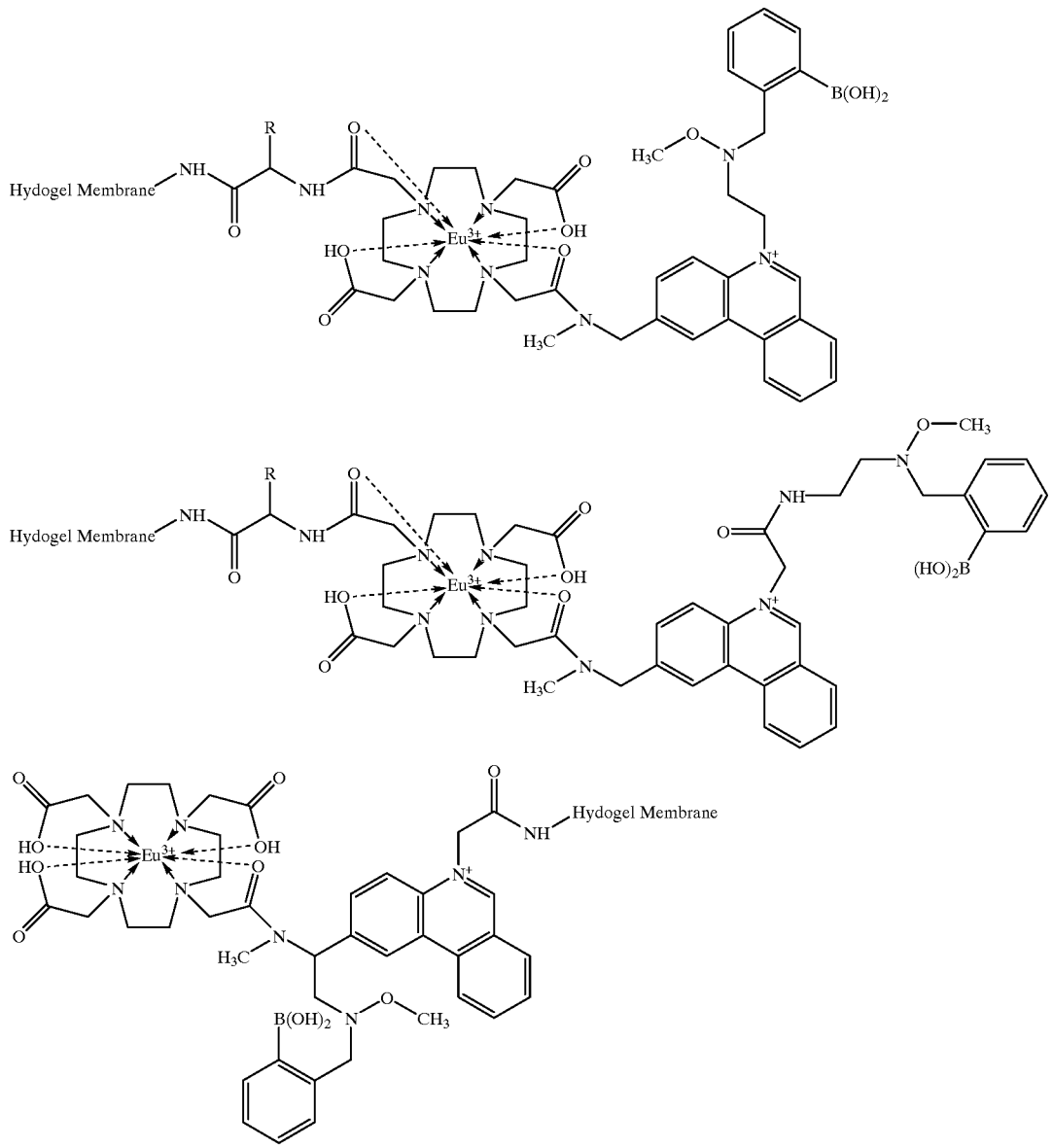

Figure 4:
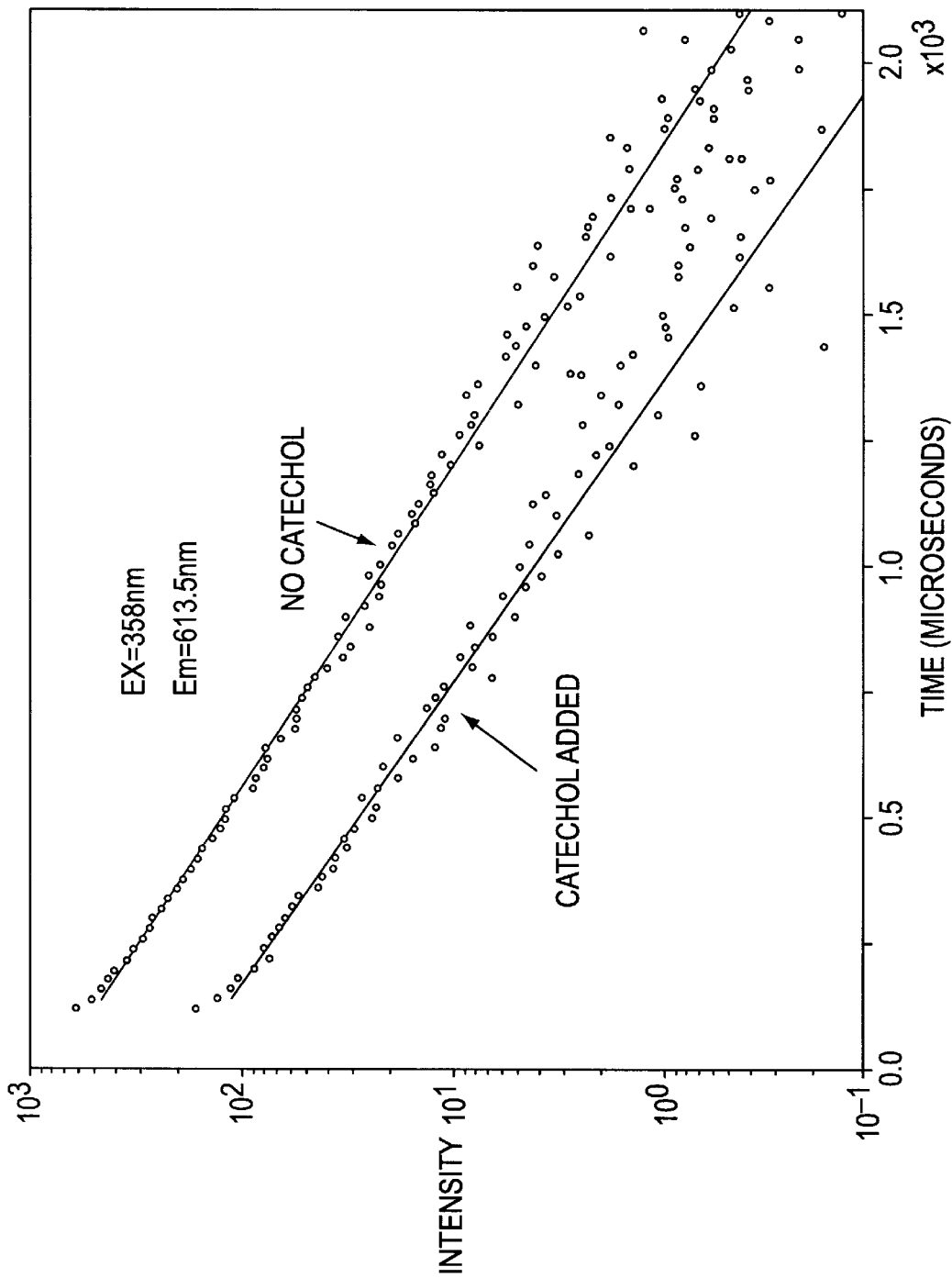
FIG. 4 illustrates the effect of adding catechol to an ethanol solution containing a boronic acid-containing europium chelate in accordance with the present invention.
Figure 5:
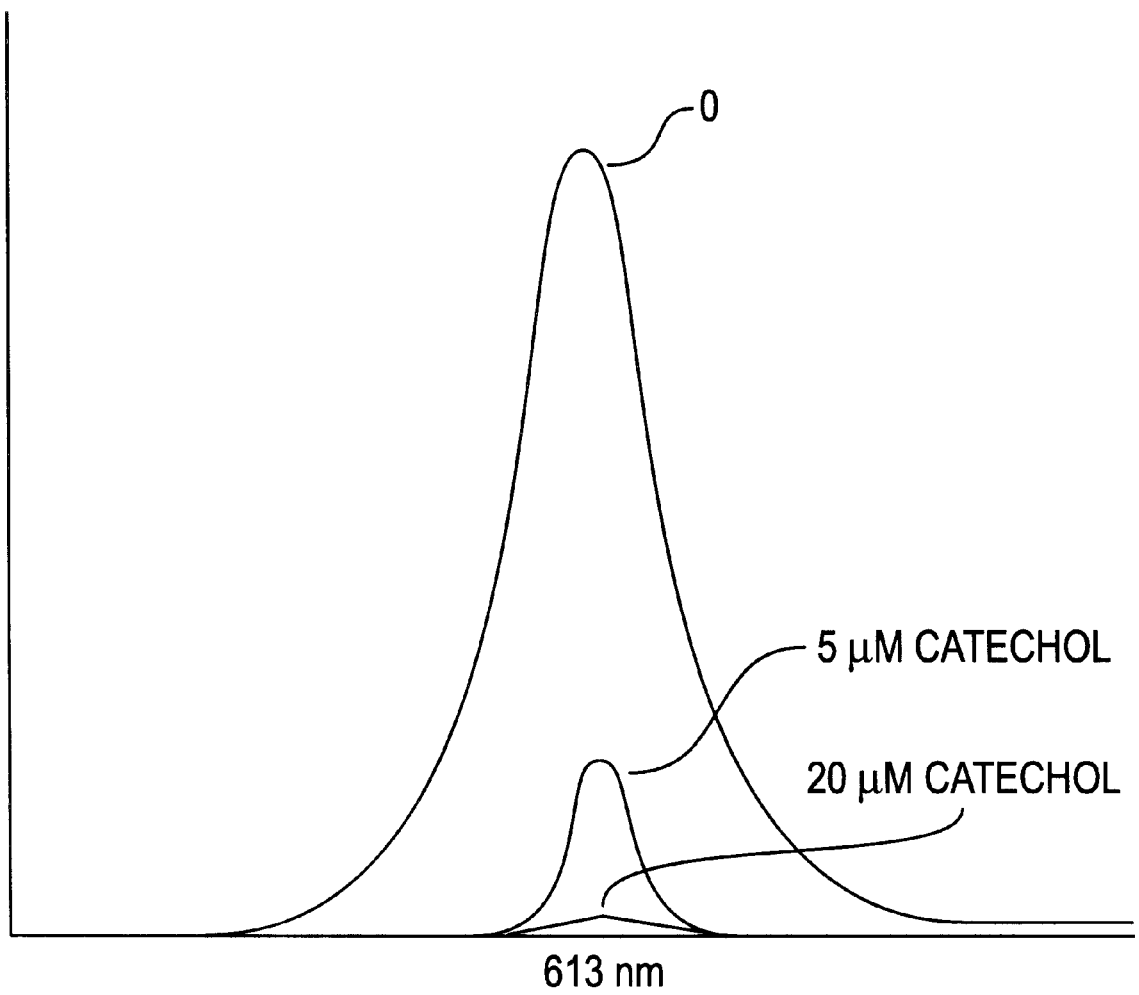
FIG. 5 illustrates the effect of catechol addition to an ethanol solution containing europium β-naphthoyltrifluoroacetate (Eu-bNTA).

As shown in FIGS. 4–5, the advantages of the present invention were demonstrated by a preferred embodiment by measuring the effect of catechol (o-dihydroxybenzene) on both the fluorescent intensity and lifetime of Eu-bNTA in an ethanol solution. The changes in fluorescent intensity detected and measured after adding catechol to the ethanol solution in the presence of Eu-bNTA are shown in FIG. 5. The fluorescent lifetime of Eu-bNTA without a boronate-containing recognition element was 362 $\mu$s ±1 $\mu$s, while the fluorescent lifetime of Eu-bNTA boronate decreased to 270 $\mu$s ±4 $\mu$s. After exposing the Eu-bNTA boronate to catechol, the fluorescent lifetime of the molecule further decreased to 209 $\mu$s ±15 $\mu$s.

Figure 3:
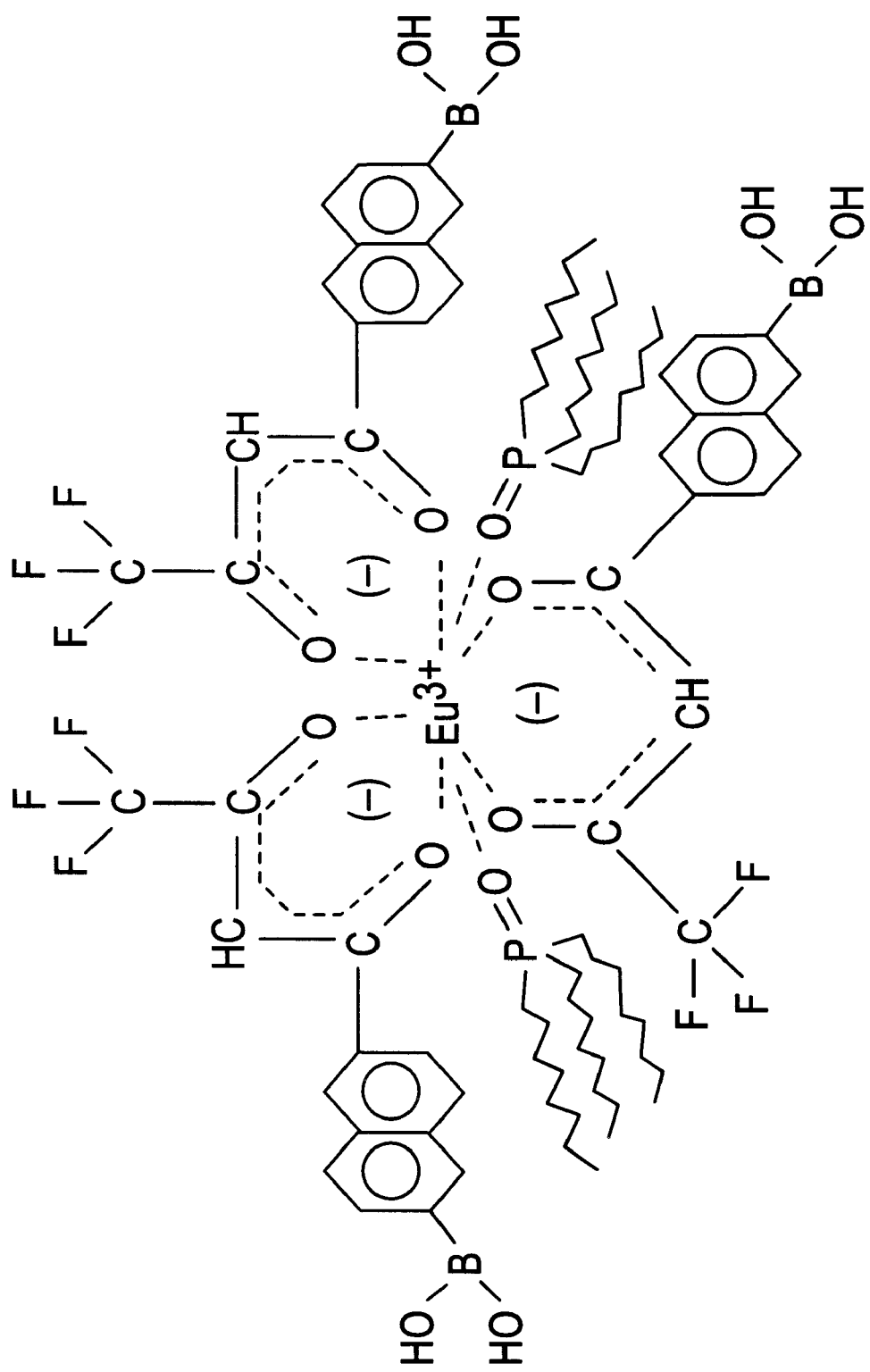
FIG. 3 illustrates a europium chelate complex containing multiple boronic acid-containing ligands in aqueous solution in the presence of trioctylphosphine oxide ("TOPO").

The effect of catechol on the fluorescent intensity and lifetime of Eu-bNTA boronate also was measured in water and was shown to quench the fluorescence of the europium ion of the chelate. Trioctylphosphine ("TOPO") was then added to protect the coordination sites located on the inner shell of the europium chelate complex from the quenching effects of the water. The addition of TOPO to the aqueous solution containing Eu-bNTA boronate is depicted in FIG. 3.

Figure 6:
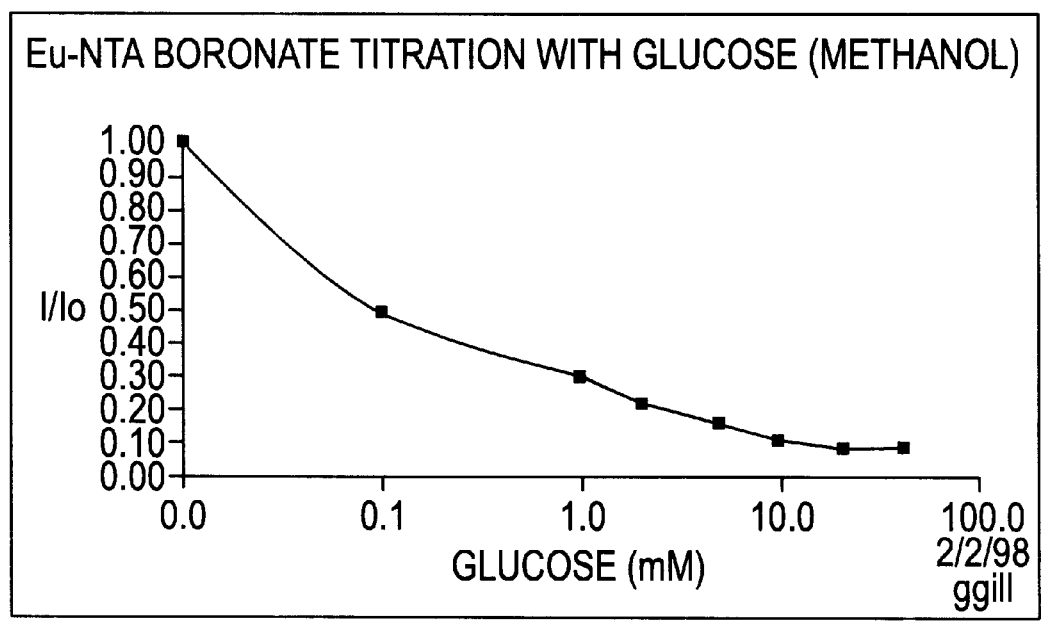
FIGS. 6–8 illustrate a Eu-NTA-boronate titration with glucose in methanol.
Figure 7:
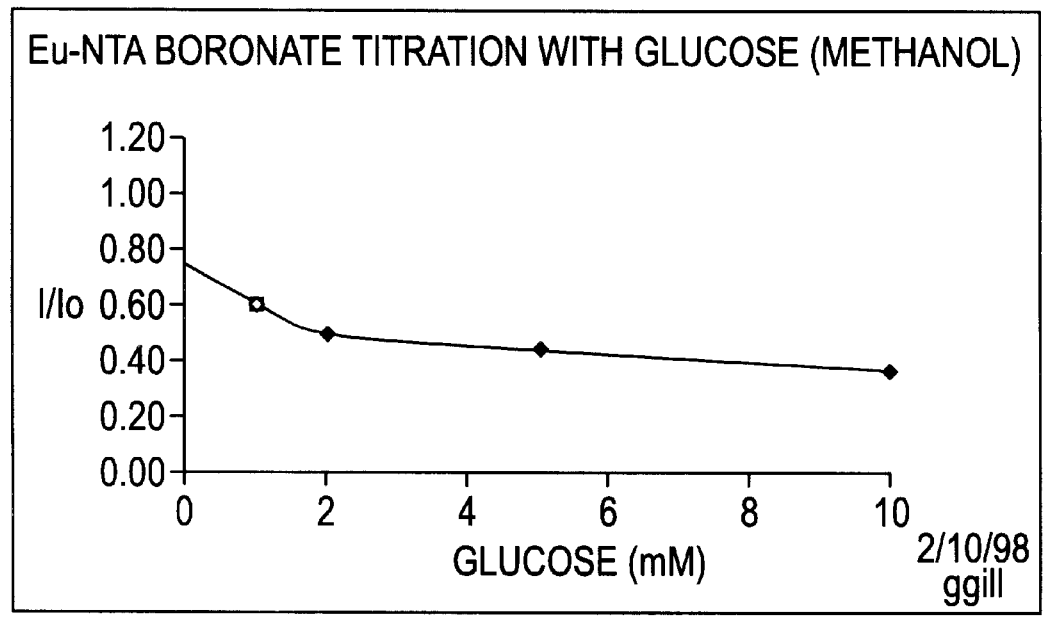
Figure 8:
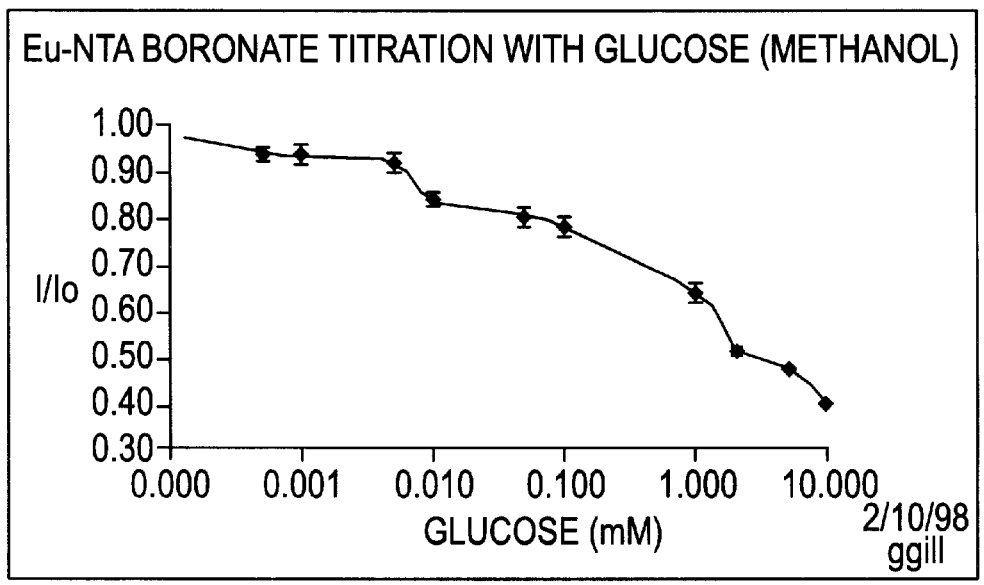

Eu-NTA boronate also was able to detect the presence of glucose in methanol. Specifically, a glucose titration with Eu-NTA boronate was performed in methanol. Data obtained from the glucose titration are shown in FIGS. 6–8. FIG. 6 depicts a Eu-NTA boronate titration against an increasing concentration of glucose. FIG. 7 depicts an expansion of the low range of the data points shown in FIG. 6. The results shown in FIG. 7 demonstrate that Eu-NTA boronate can detect the presence of glucose at concentrations well below normal physiological levels of approximately 4.7 mMol. Shown by the data plot in FIG. 7, differences in glucose concentrations can be discriminated within the physiological range of less than about 0.5 mMol. Although FIG. 7, because of the close proximity of data points below 0.001 mMol glucose, does not show the lower end sensitivity of Eu-bNTA boronate to changes in glucose concentration, FIG. 8 plots the low range of FIG. 7 as the semi-log plot of glucose concentration versus $I/I_o$.

Figure 9:
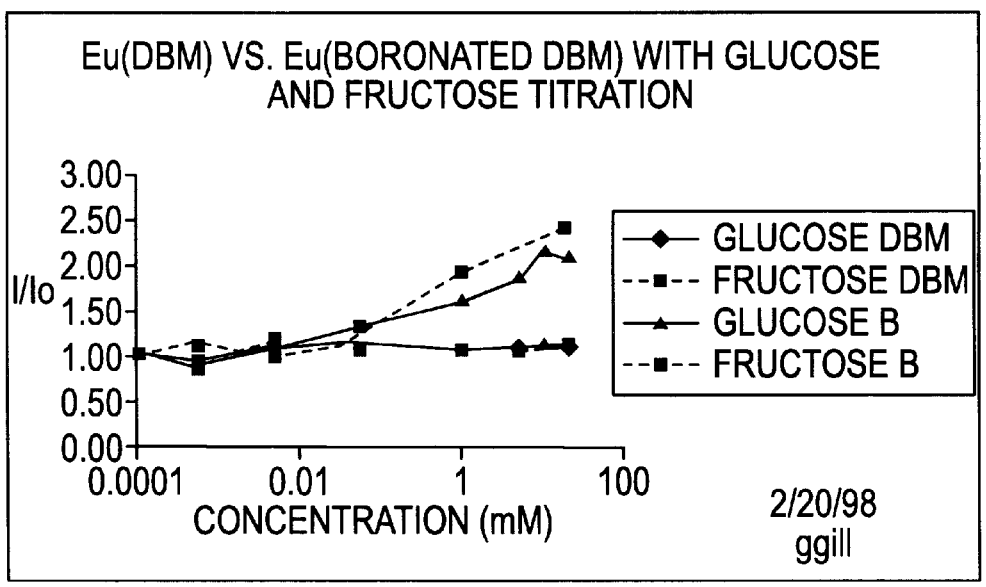
FIG. 9 illustrates a comparison between a europium dibenzoylmethane (Eu(DBM)) and Eu(boronated DBM) titration with glucose and fructose in methanol.
Figure 10A:
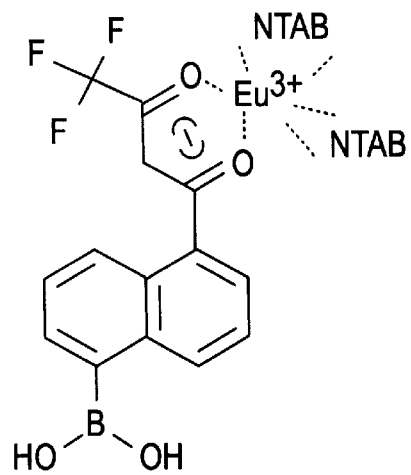
FIG. 10 illustrates an Eu-NTA boronate titration with glucose in methanol.
Figure 10B:
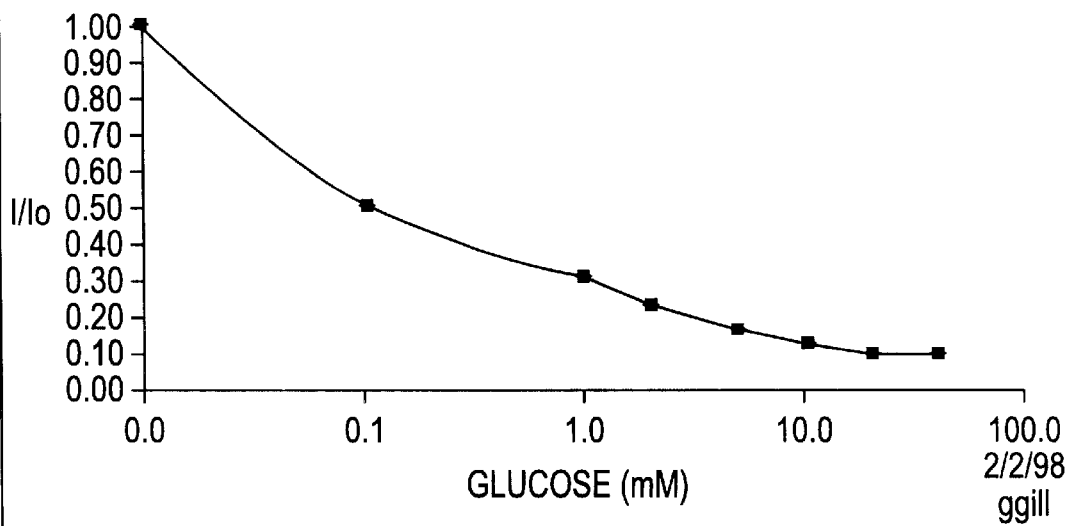
Figure 11A:
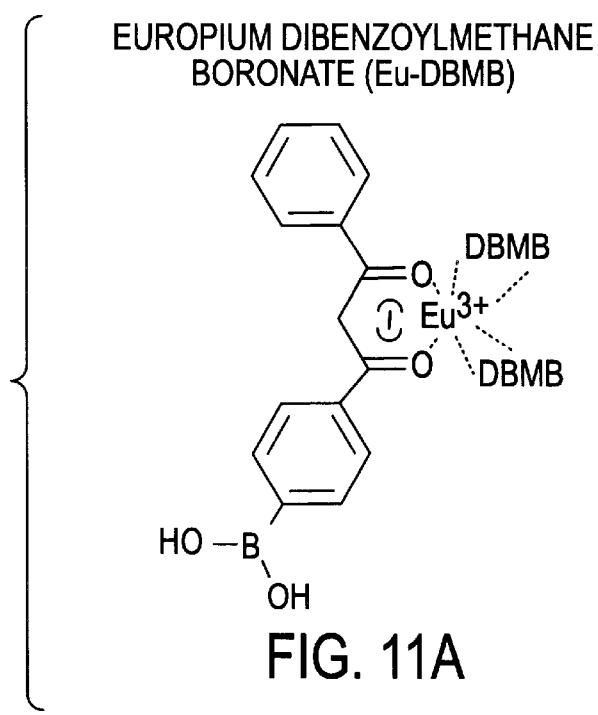
FIG. 11 illustrates an Eu-DBM boronate titration with glucose and fructose in methanol.
Figure 11B:
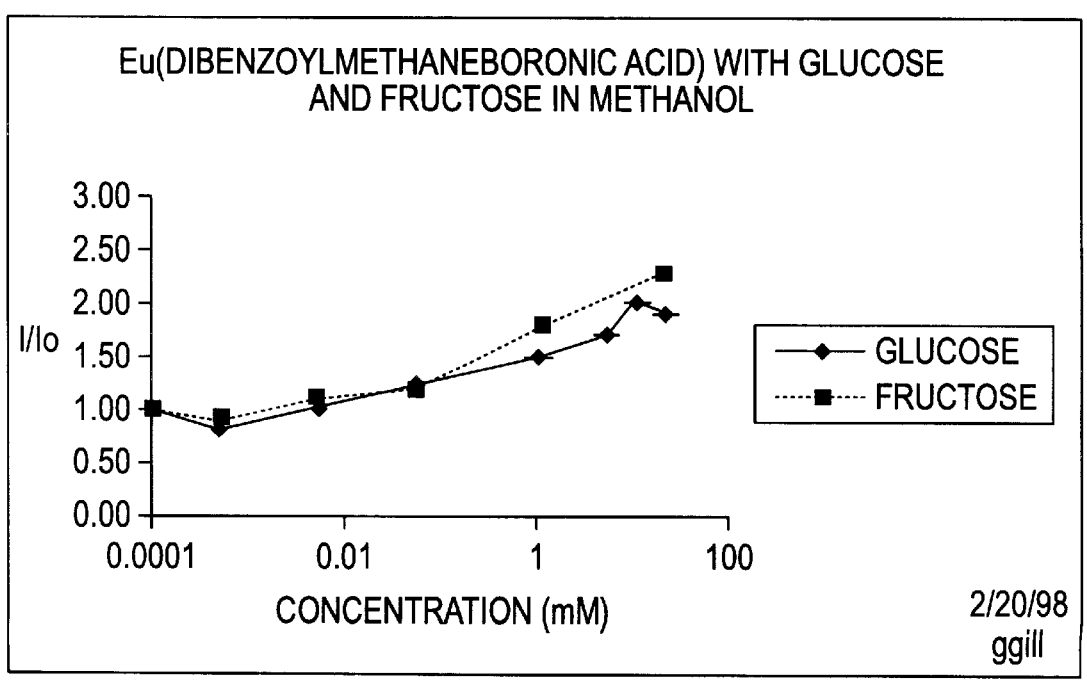
Figure 12A:
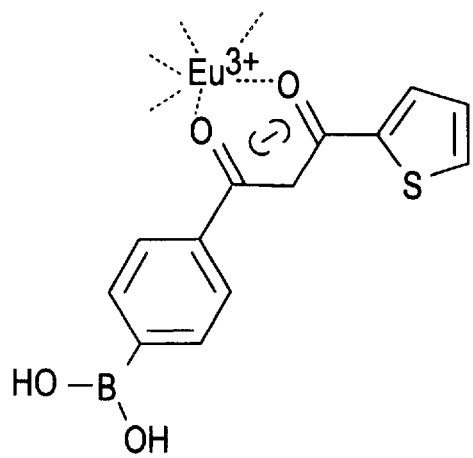
FIG. 12 illustrates an Eu(theonyl-4-benzoylmethaneboronic acid) titration with glucose and fructose in methanol.
Figure 12B:
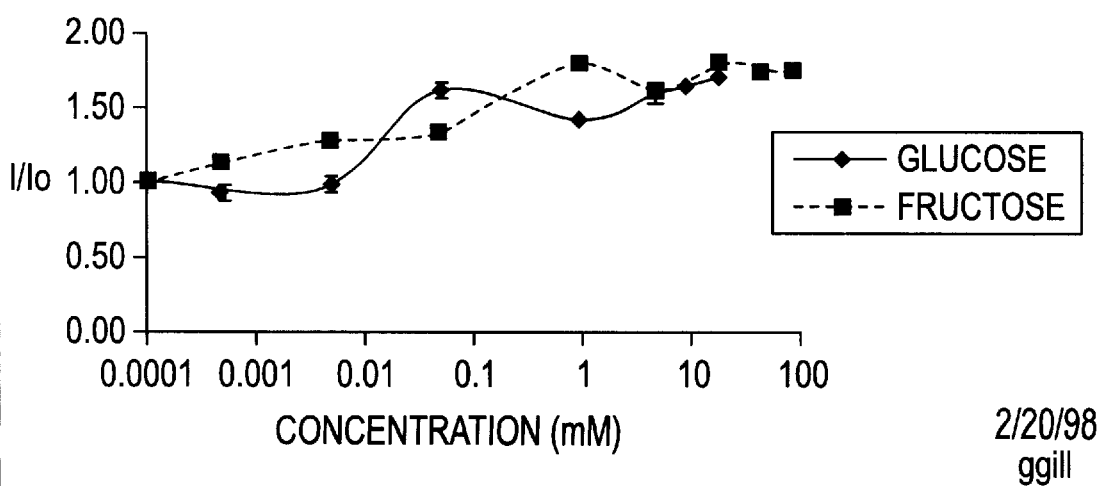
Figure 13A:
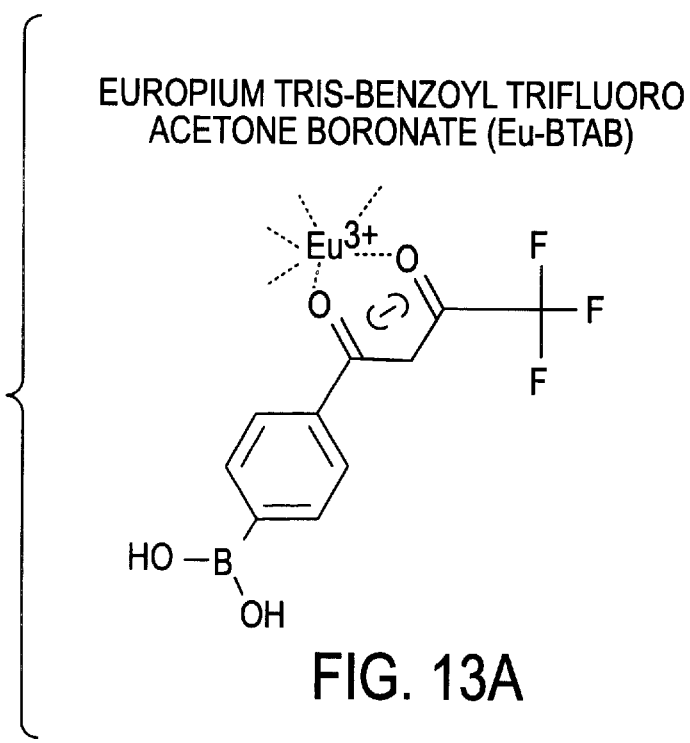
FIG. 13 illustrates an Eu(benzoyl-trifluoromethylacetoneboronic acid) titration with glucose and fructose in methanol.
Figure 13B:
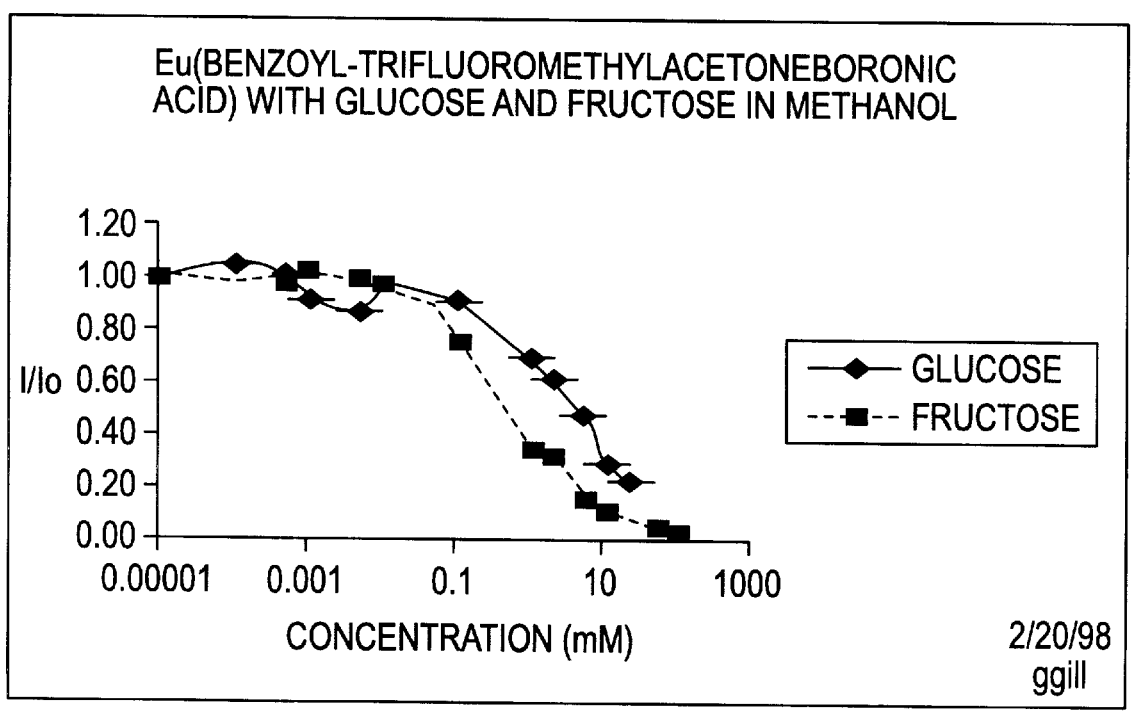

FIG. 9 shows the results of titrating europium dibenzoyl-methane (Eu(DBM)) and Eu(boronated DBM) separately with glucose and fructose in methanol. Specifically, glucose and fructose concentrations were varied as 0.0005, 0.005, 0.05, 1, 5, 10 and 20 mM. The data plots for glucose B and fructose B in FIG. 9 represent glucose and fructose titrations of Eu(boronated DBM). It is readily seen from the results in FIG. 9 that the fluorescent intensity of boronated europium dibenzoylmethane increases significantly when exposed to concentrations of glucose and fructose above about 0.01 mM, while the fluorescent intensity of the non-boronated Eu(DBM) does not change to any notable extent upon the addition of glucose and fructose. Without a specific recognition element (e.g., a boronate), the lanthanide metal chelate complex is not responsive to the presence of glucose, fructose or other cis-diol compounds. Accordingly, with an analyte-specific recognition element, in this example a boronate group, the lanthanide chelate complex of this invention is sensitive to the presence of glucose, fructose and other cis-diol compounds, and thus can be utilized to detect the presence or concentration of such and other analytes.

FIGS. 10–13 further demonstrate the ability of lanthanide metal chelate complexes in accordance with the present invention to detect the presence or concentration of glucose and/or fructose in a sample.

As stated above, the fluorescent indicator molecules of the present invention can be used in many different types of fluorescent sensors. The fluorescent indicator molecules can be used in the sensors to detect the presence or concentration of an analyte such as glucose or other cis-diol compound in a sample such as a liquid sample, including a biological fluid, and more specifically a human fluid. For example, fluorescent indicator molecules in accordance with the present invention can be dispersed in a polymer matrix which is permeable to glucose or other cis-diol compound. The presence or concentration of glucose or other cis-diol compound in a medium such as a liquid medium can then be determined by measuring the change in intensity or lifetime of fluorescence emitted by the indicator molecule after binding to glucose or other cis-diol compound through one or more boronate-containing recognition elements.

U.S. Pat. No. 5,517,313, the disclosure of which is incorporated herein by reference, describes a fluorescence sensing device in which the fluorescent indicator molecules of the present invention can be used to determine the presence or concentration of an analyte such as glucose or other cis-diol compound in a liquid medium. The sensing device comprises a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source.

The fluorescence of the indicator molecules employed in the device described in U.S. Pat. No. 5,517,313 is modulated, e.g., attenuated or enhanced, by the local presence of an analyte such as glucose or other cis-diol compound.

In the sensor described in U.S. Pat. No. 5,517,313, the material which contains the indicator molecule is permeable to the analyte. Thus, the analyte can diffuse into the material from the surrounding test medium, thereby effecting the fluorescence emitted by the indicator molecules. The light source, indicator molecule-containing material, high-pass filter and photodetector are configured such that at least a portion of the fluorescence emitted by the indicator molecules impacts the photodetector, generating an electrical signal which is indicative of the concentration of the analyte (e.g., glucose) in the surrounding medium.

In accordance with other possible embodiments for using the fluorescent indicator molecules of the present invention, fluorescence sensing devices also are described in co-pending U.S. patent application Ser. Nos. 08/855,234, 08/855,235, and 08/855,236, all incorporated herein by reference.

The fluorescent indicator molecules of the present invention can be prepared by persons skilled in the art without an undue amount of experimentation using readily known reaction mechanisms and reagents, including reaction mechanisms which are consistent with the general procedures described below.

Preparation of Boronated Europium Tetrakis β-Diketone Complexes

1. Naphthalene-1-boronic acid, as available from Frontier Scientific (Logan, Utah), is dissolved in toluene.

2. The boronic acid must first be protected (capped) by reacting it with 2,2-dimethyl-1,3-propanediol (Aldrich Chemical Company) while azeotropically removing water by using a Dean-Stark trap to provide 2,2-dimethylpropane-1,3-diyl 1-naphthylboronate, as shown below:

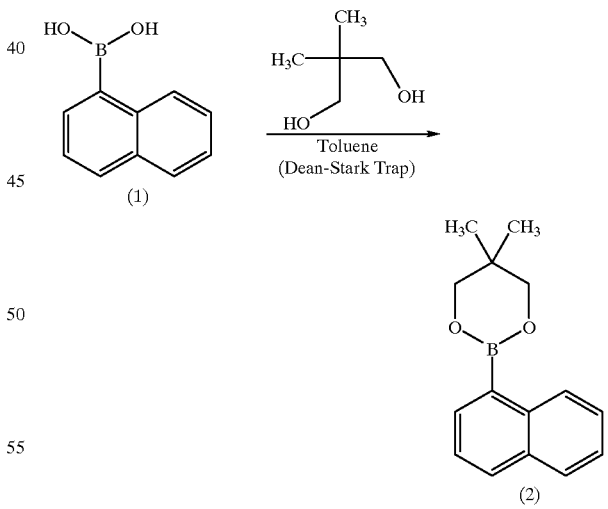

3. The capped boronic acid can then be acylated by Friedel-Crafts acetylation by reacting the boronic acid with acetic anhydride and aluminum trichloride in anhydrous carbon disulfide to produce 2,2-dimethylpropane-1,3-diyl 5-acetyl-1-naphthylboronate. An approximately 70% yield of the reaction product, which appears as a viscous liquid, will typically result, as shown below:

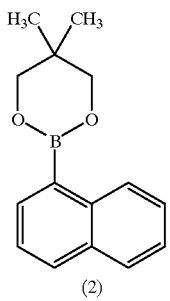

(2)

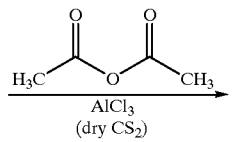

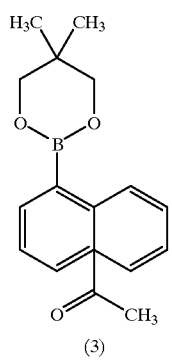

(3)

4. The β-diketone can then be formed and the boronate can be decapped by a Claisen condensation between (3) and ethyl trifluoroacetate (Aldrich) using sodium methoxide (in dry ether) as the condensing agent, as shown below:

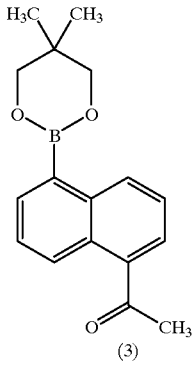

(3)

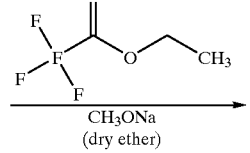

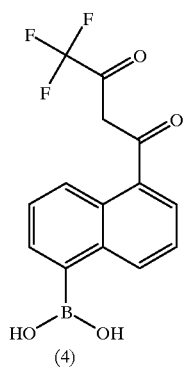

(4)

5. The intermediate product (4), 5-naphthoyl-trifluoroacetoneboronic acid, can then be purified by preparative silica gel TLC while eluting with methylene chloride. In at least one preparation, the third band elution (Rf=0.70–0.85) was recovered from the plate and analyzed by proton NMR at 400 MHZ. The NMR spectrum exhibited a pattern which was characteristic of the enol form of the β-diketone, specifically showing peaks at sigma 6.69 (singlet) and at sigma 15.28 (broad singlet).

6. The final europium tetrakis indicator complex containing a boronate group as the analyte-specific recognition element is produced by reacting the β-diketone (4), with europium trichloride hexahydrate (Aldrich) and piperidine in absolute ethanol, as shown below:

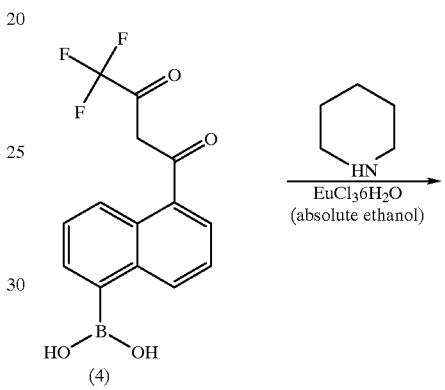

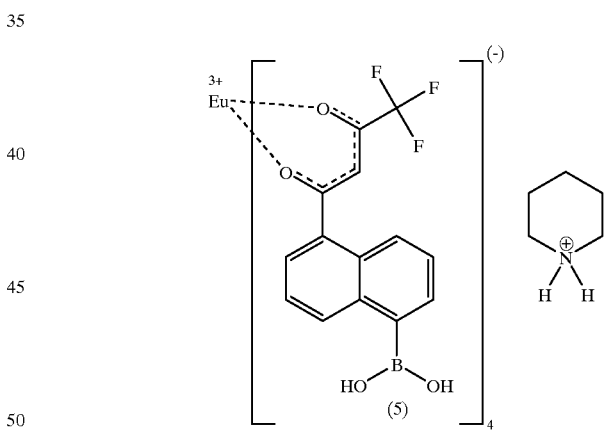

The solution is then heated to 70° C. for three hours. After heating, the resultant solution shows a characteristic orange-red emission upon irradiation with a handheld, long-wave UV source. Additionally, a fluorescence scan with a Shimadzu fluorometer shows a peak excitation wavelength of 340 nanometers and a europium complex characteristic peak emission wavelength of 613 nanometers.

Other synthetic schemes for preparing compounds useful in the present invention are depicted below.

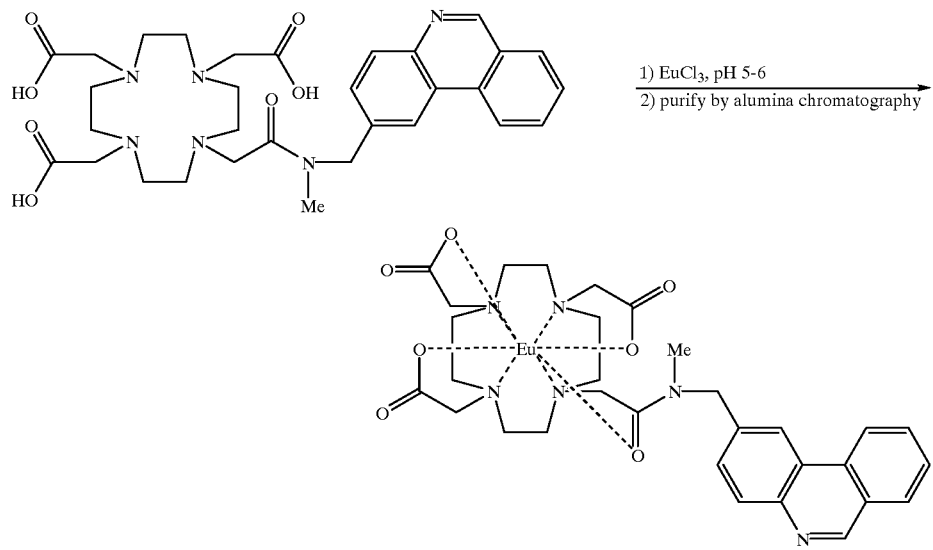
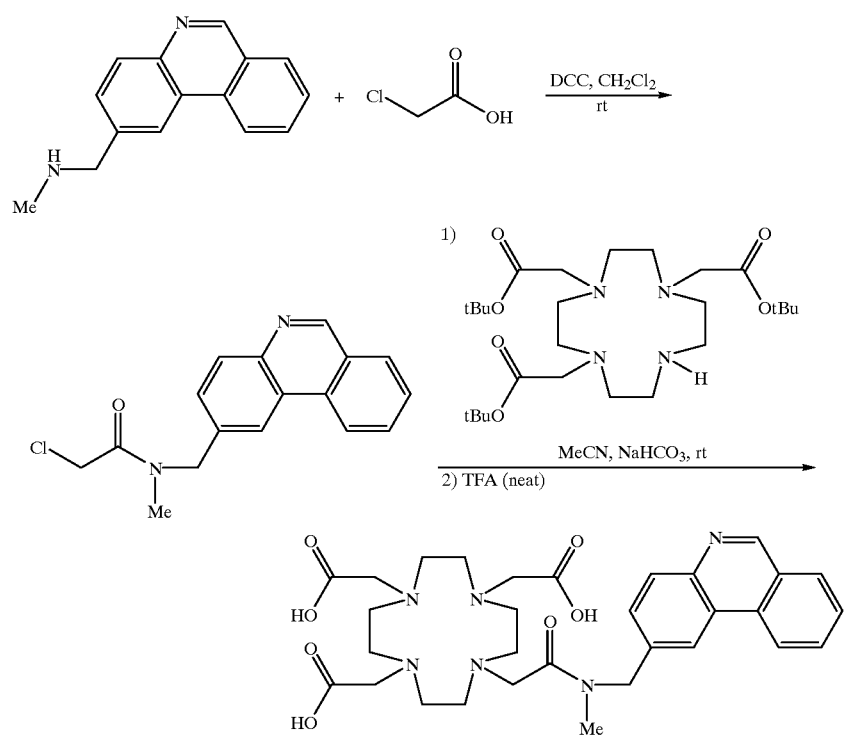
Sythesis for Target A Intermediate
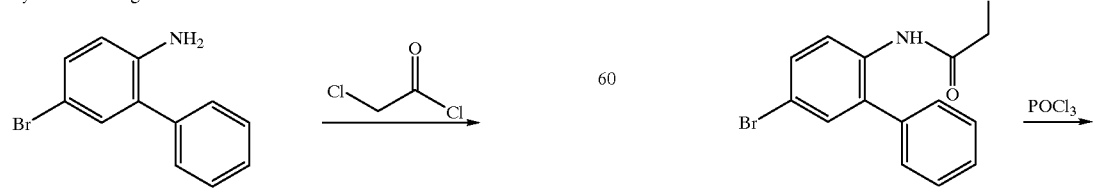

39
-continued
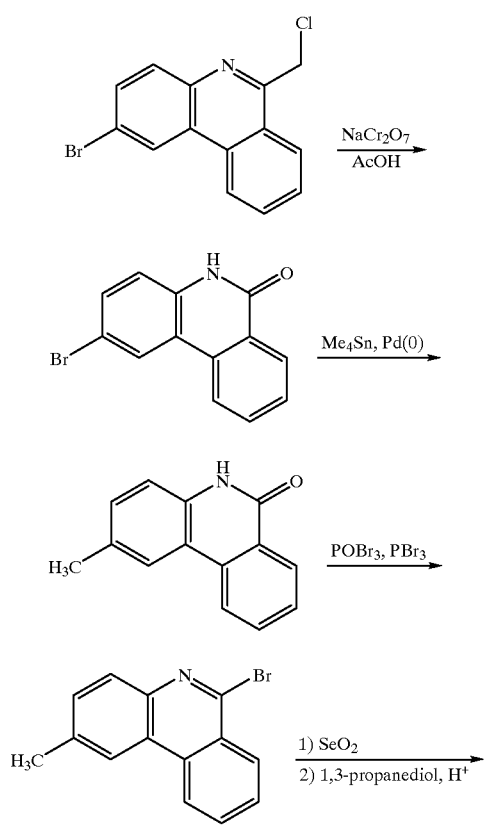
40
-continued
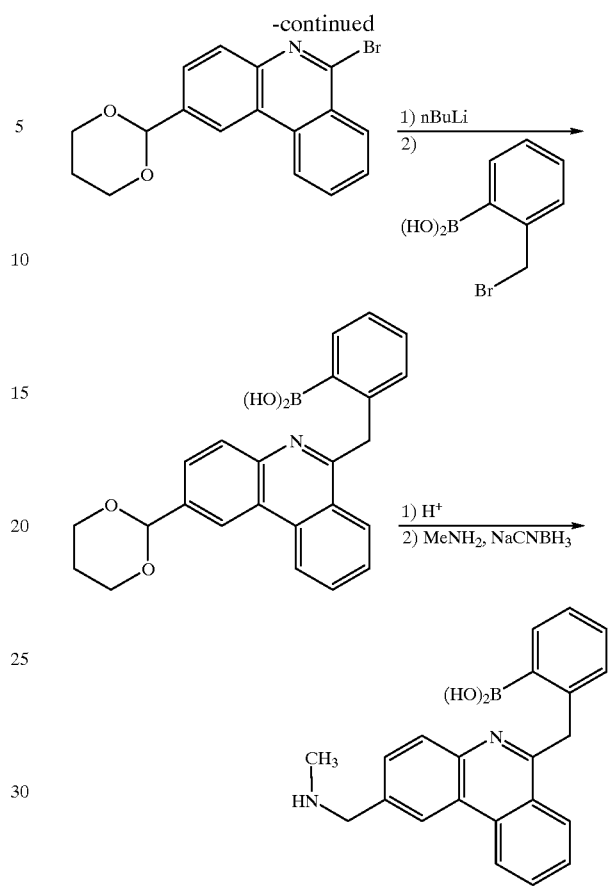
Synthesis for Target B-1, C-1 Intermediates
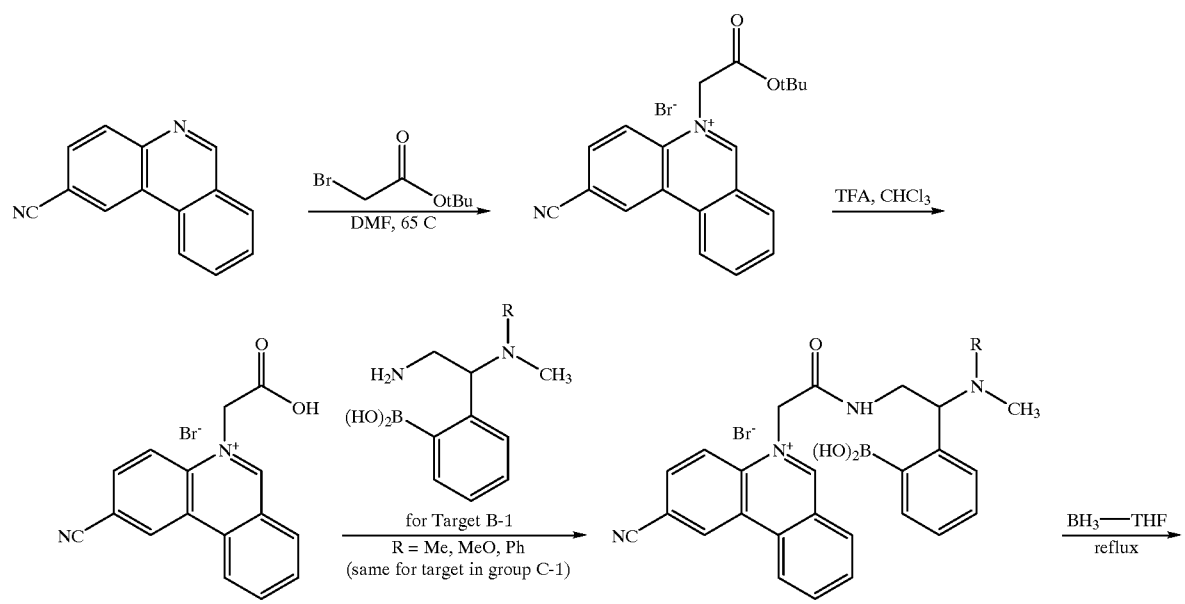

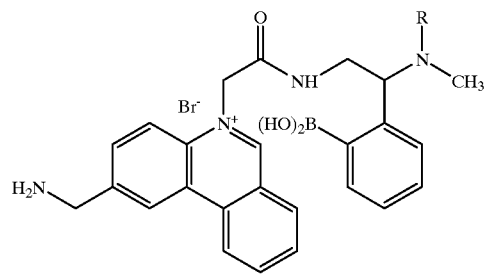
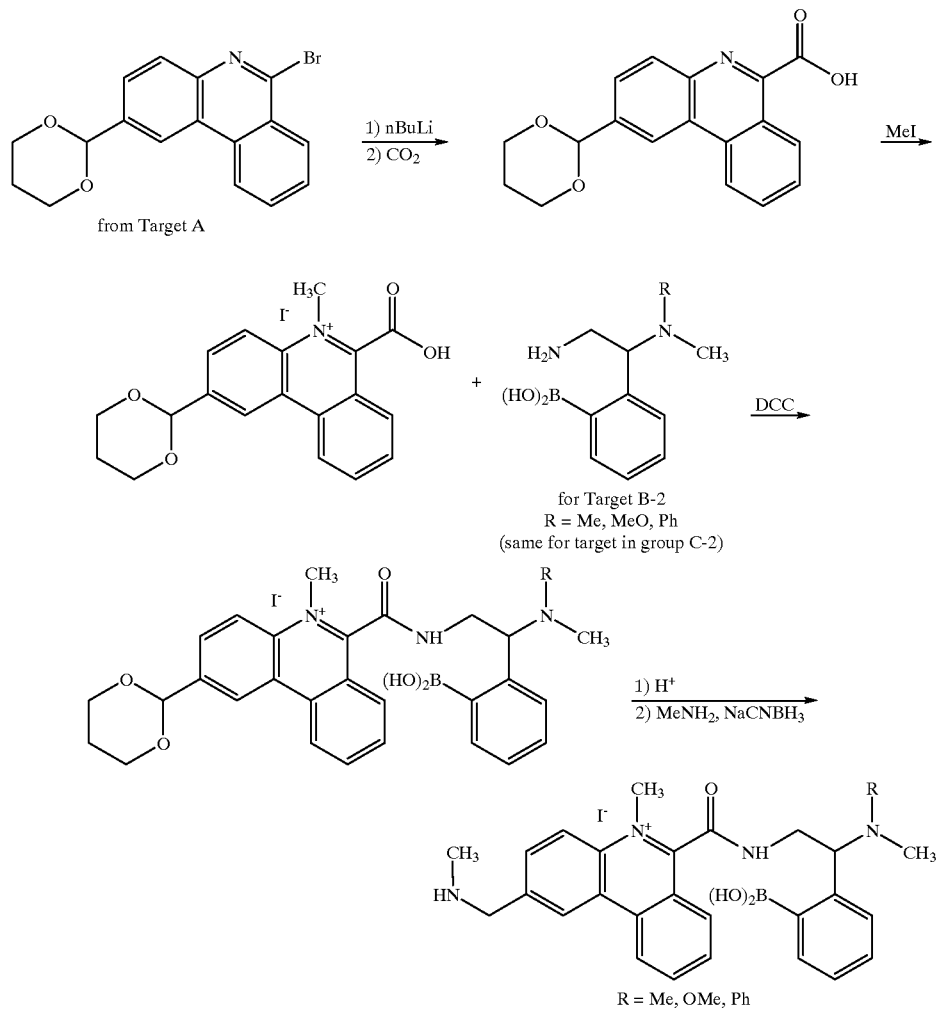
Synthesis for Target B-2, C-2 Intermediates
Synthesis for Target E Intermediate
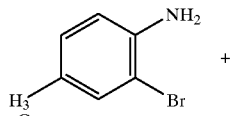
-continued
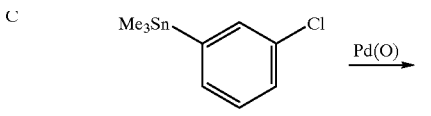

-continued
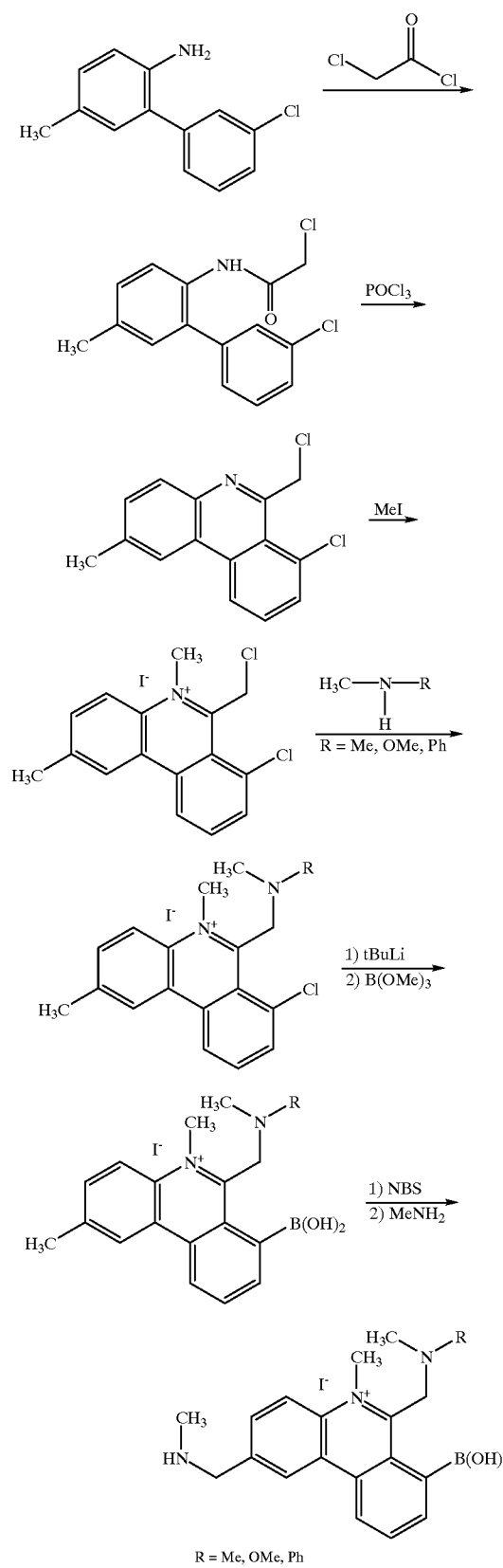
R = Me, OMe, Ph
Synthesis for Target EEE Intermediate
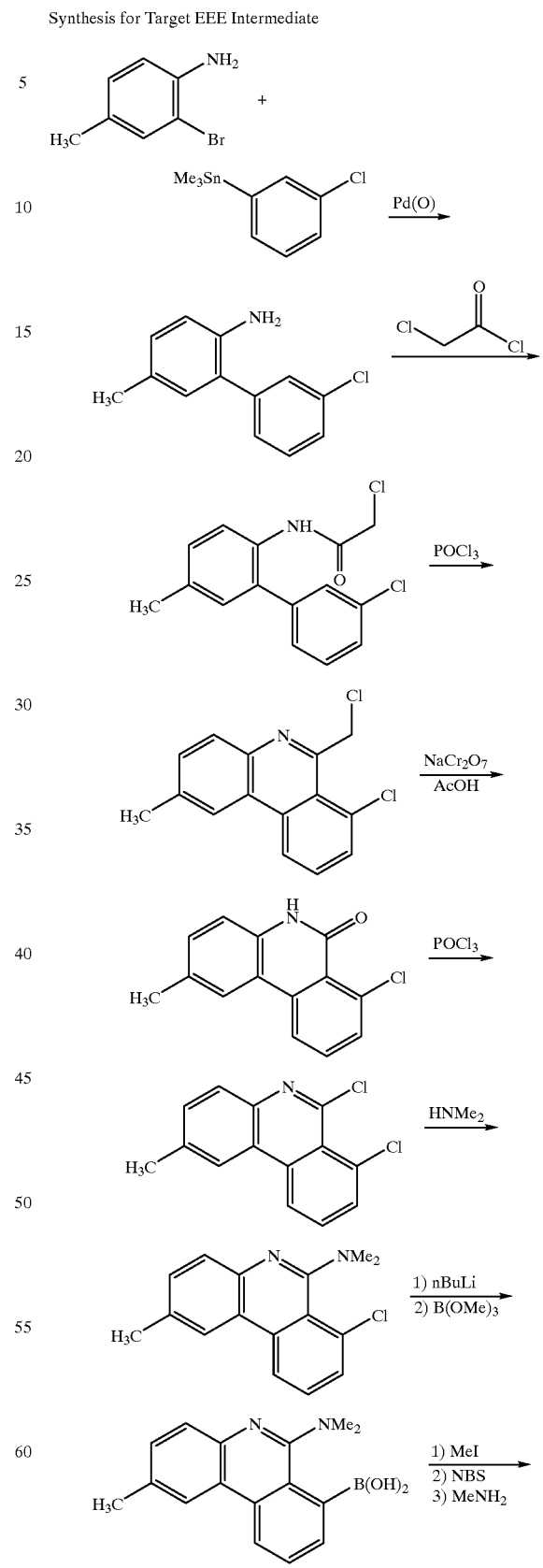

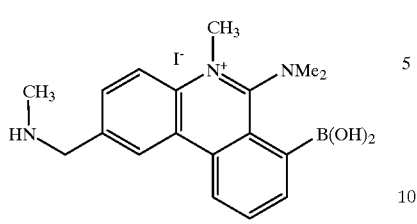
Synthesis for Target F Intermediate
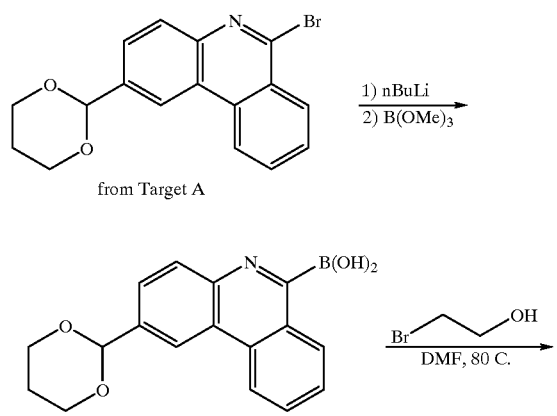
from Target A
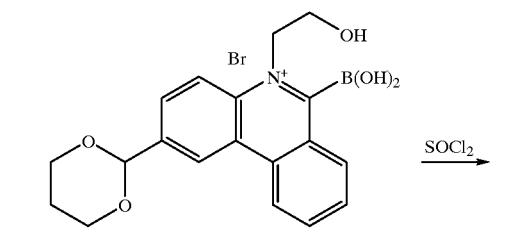
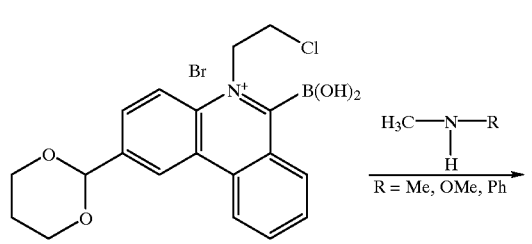
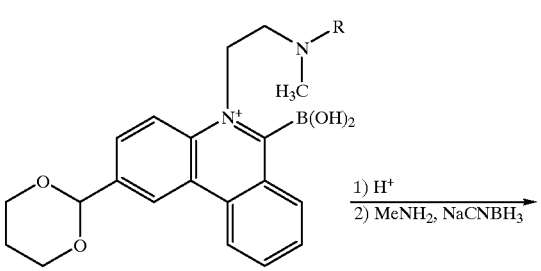
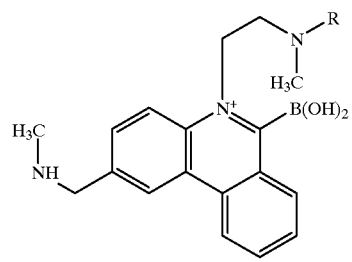
Target F
R = Me, OMe, Ph
Target H - Synthesis
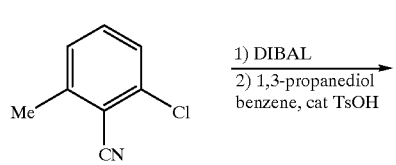
Aldrich Chemical Co.
St. Louis, MO
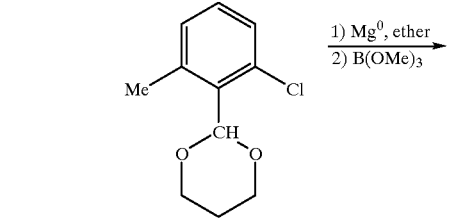
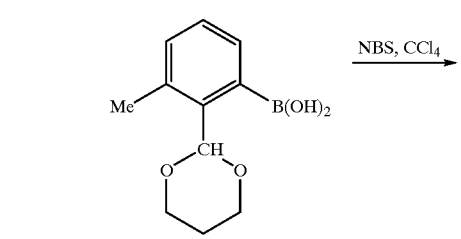
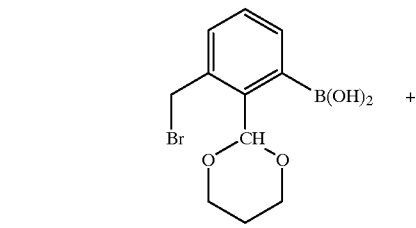
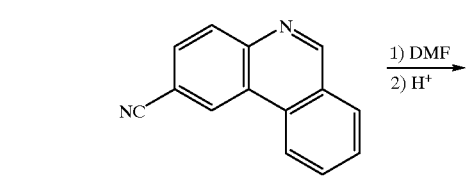

47
-continued
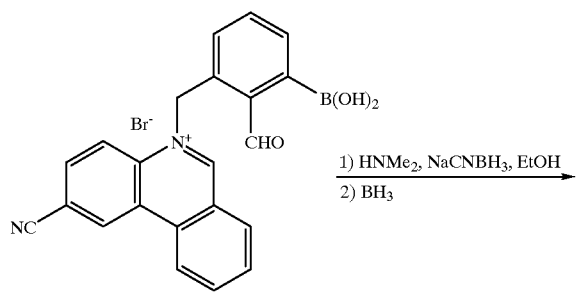
48
-continued
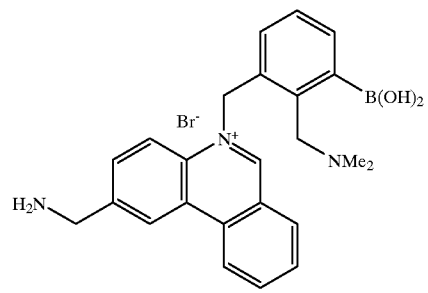
Synthetic Scheme for Approach 3
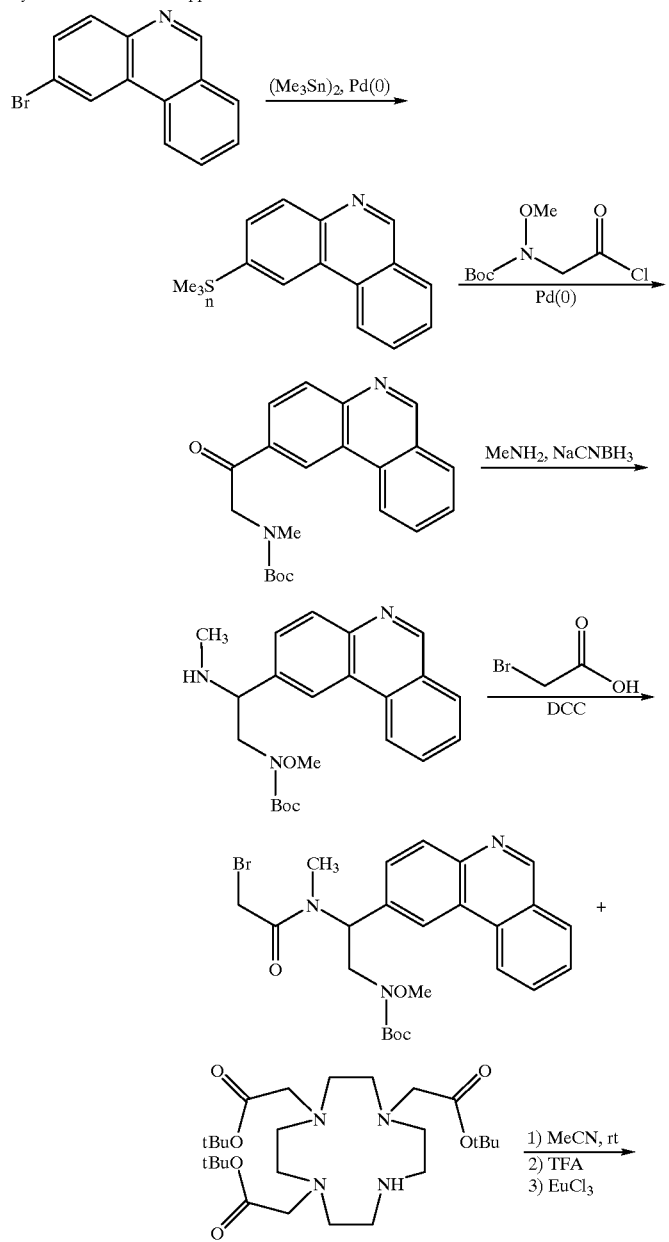

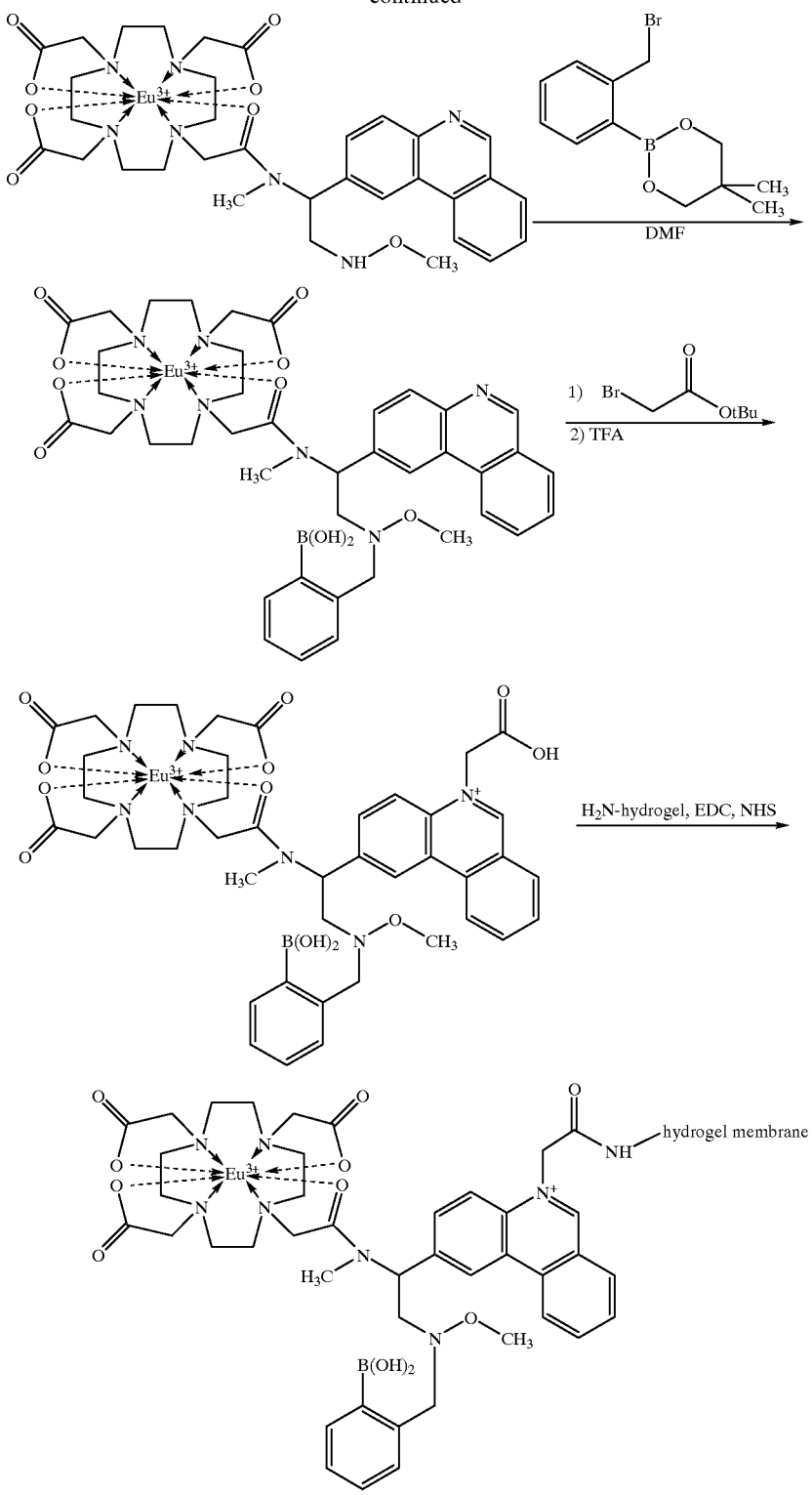
For additional details concerning aspects of the synthesis schemes depicted above, see the following publications, the contents of which are incorporated herein by reference:
1. Walls, L. P., *JCS*, (1934), 104–109
2. Reese, C. B., *JCS*, (1958), 895–901
3. Muth, C. W. et. al., *J. Medicinal Chem*, (1973), Vol 16, No. 3, 1973
4. Badger, G. M., et. al., *J.C.S.*, (1951), 3207–3211
5. Ishiyama, T., et. al., *J. Org. Chem.* (1995), 60, 7508–7510
6. Forrester, A. R., et. al., *J.C.S. Perkin I*, 612–615

7. Petterson, R. C., et. al., *J. Org. Chem.*, (1974), Vol. 39, No. 13, 1841–1845
8. Nagarajan, K., et. al., *Indian Journal of Chemistry*, Vol. 11, Febuary 1974, 112–114
9. Hollingsworth, B. L., et. al., *J. Chem. Soc.*, (1961), 3771–3773
10. Finkelstein, J., et. al., *J. Amer. Chem. Soc.*, (1951), Vol 73, 302–304
11. Parker, D., et. al., *J. Chem. Soc., Chem. Commun.*, (1997) 1777–78
12. Stille, J. K., *Angew, Chem. Int. Ed. Engl.*, (1986), Vol 25, 508–524
13. Sherry, A. D., et. al., *Inorganica Chimica Acta*, (1987), Vol. 139, 137–139
14. Bansal, N., et. al., *J. Magnetic resonance Imaging*, (1992) Vol. 2, 385–391
15. Sherry, A. D., et. al., *J. Magnetic Resonance*, (1988), Vol 76, 528–533

The invention is illustrated by the following examples for further understanding thereof.

EXAMPLE I

Detection of Glucose and Fructose with Eu(4-dibenzoylmethaneboronic acid)

25 $\mu$l of 6.5 mM Eu(4-dibenzoylmethaneboronic acid)$_4$ PyCl was added to 525 $\mu$l methanol and vortexed. From stock solutions in methanol (4 $\mu$M, 400 $\mu$M, 4 mM and 40 mM), samples of glucose and fructose were separately prepared at concentrations of 0.5 $\mu$M, 5 $\mu$M, 50 $\mu$M, 1 mM, 5 mM, 10 mM, and 20 mM for each of the two sugars. The results of which are shown in FIG. 9, the fluorescence emission intensity of the Eu chelate complex at 613 nm was monitored for each of the separate samples of glucose and fructose after exciting the Eu chelate complex at the required excitation wavelength of 365 nm.

EXAMPLE II

Synthesis of Europium Tetrakis—5-naphthoyl-trifluoroacetoneboronic Acid

I. Preparation of 2,2-dimethylpropane-1,3-diyl-1-naphthylboronate (1)

The boronate group of the precursor is protected from any potential adverse effects caused by subsequent reaction conditions during synthesis of the europium chelate complex according to the following procedure:

Naphthalene-1-boronic acid (15.2 grams, 0.0884 moles) and 2,2-dimethyl-1,3-propanediol (10.0 grams, 0.0960 moles, 1.1 equivalents) were refluxed in toluene (200 ml) while removing water azeotropically using a Dean-Stark trap for 28 hours. The toluene was then evaporated by simple distillation, followed by aspirator pressure distillation while heating for 2 hours until reaching a temperature of about 80° C. The unreacted 2,2-dimethyl-1,3-propanediol was then removed under vacuum (0.5 mm) while heating up to 60° C. for 1 hour. A white solid (20.94 grams, 99% purity) of 2,2-dimethylpropane-1,3-diyl-1-naphthylboronate was obtained.

The product was verified by $^1$HNMR (CDCl$_3$, 400 MHz).

II. Friedel-Crafts Acetylation: Preparation of 2,2-dimethylpropane-1,3-diyl-5-acetyl-1-naphthylboronate (2)

An acetyl group was introduced into the aromatic structure of the precursor to form a diketone, according to the following procedure:

2,2-dimethylpropane-1,3-diyl-1-naphthylboronate (1) (21.0 grams, 0.0878 moles) was dissolved in 150 ml of dry carbon disulfide while stirring in a 250 ml round bottom flask in an ice water bath. Separate portions of aluminum trichloride (28.7 grams, 0.215 moles) were added over a period of two hours. The mixture was then stirred and slowly warmed to room temperature over a period of one hour. A sticky, dark, semisolid was seen deposited inside the flask. The mixture was cooled again in an ice water bath, whereafter a refluxing condenser was added to the flask. Acetic anhydride (8.93 grams, 0.0875 moles) was then added over a period of 2 hours. The mixture was then warmed to 40° C. to initiate the reaction. During addition of the acetic anhydride, it was necessary to agitate the reaction mixture (by hand swirling) occasionally, as to control any exothermic reaction which might occur during the reaction.

After allowing the reaction mixture to sit at room temperature for 2 hours, the mixture was then heated slowly to 50° C. over a period of 1 hour and maintained at that temperature for three hours. A dark solid was observed to form in the reaction mixture.

800 ml of ice water, 15 ml of concentrated hydrogen chloride and 250 ml of methylene chloride were then used together to decompose and extract the reaction mixture into two clear layers. The bottom organic layer was then collected, dried over sodium sulfate, and evaporated at reduced pressure up to 80° C. for three hours to yield 19.39 g of dimethylpropane-1,3-diyl-5-acetyl-1-naphthylboronate (2) in a semisolid form, having a yield of 78%.

III. Claisen Condensation: Preparation of 5-naphthoyl-trifluoroacetoneboronic acid (3)

A $\beta$-diketone ligand was formed, as follows:

A mixture of sodium hydride was reacted with 2 ml of methanol (0.313 gram, 0.01302 moles) in 10 ml of dry ether. The resulting solution was dried under reduced pressure up to 100° C. for two hours to yield sodium methoxide in a solid form. The sodium methoxide was then treated with 45 ml of dry ether and cooled in an ice water bath. Ethyl trifluoroacetate (1.763 grams, 0.0124 moles) was then added, followed 10 minutes later by adding a solution of dimethylpropane-1,3-diyl-5-acetyl-1-naphthylboronate (2) (3.50 grams, 0.0124 moles) in 20 ml of dry ether, which solution was added dropwise over a period of another 10 minutes. The mixture was then stirred for 30 minutes at room temperature and heated to reflux for 70 hours. While stirring the mixture in an ice water bath, 25 ml of water and 8 ml of 10% hydrogen chloride were added to acidify the water layer to a pH of 1. Two clear layers thereafter appeared in the flask.

The top etheral layer was then collected, dried over sodium sulfate, and evaporated under reduced pressure up to 60° C. for 1 hour to yield the $\beta$-diketone in a dark liquid form (4.36 grams). The resultant $\beta$-diketone was purified by preparative silica gel TLC by eluting with methylene chloride. The third band (Rf=0.70–0.85) was recovered from the TLC plate as a 25% yield of 5-naphthoyl-trifluoroacetoneboronic acid (3) (1.20 grams).

The product was verified by proton NMR (400 MHZ) spectra having a pattern characteristic of the enol form of the $\beta$-diketone with peaks at sigma 6.69 (singlet) and at sigma 15.28 (broad singlet).

IV. Chelation/Complexation: Formation of the europium-(beta-diketoneboronic acid) tetrakis complex (4)

The lanthanide chelate complex for use as a fluorescent indicator molecule was then produced as follows:

A solution of europium trichloride hexahydrate (0.7 mg, 0.0019 mmoles) in 0.5 ml absolute ethanol was added to a solution of 5-naphthoyl-trifluoroacetoneboronic acid (3) (2.2 mg, 0.0058 mmole) and piperidine (130 mg) in 0.5 ml of absolute ethanol. This mixture was heated slowly to 70° C. over a period of 2 hours and maintained at that temperature for an additional 3 hours to form the europium tetrakis complex (4).

The resultant solution exhibited a characteristic orange-red emission upon irradiation with a hand-held, long wave UV source. Additionally, a fluorescence spectra, as measured with a Shimadzu fluorometer, showed a peak excitation wavelength of 340 nanometers and an emission pattern characteristic of a europium chelate complex of 613 nanometers.

The invention has been described in connection with certain preferred embodiments. Those skilled in the art will recognize that modifications and improvements may be made without departing from the spirit and scope of the invention.

What is claimed is:

1. An indicator molecule for detecting the concentration of an unlabeled analyte, comprising a fluorescent lanthanide metal chelate complex having the formula:

$$M(-Ch(-R_X))_Y$$

wherein:

M is a lanthanide metal ion; Ch is a chelator comprising a ligand; R is an analyte-specific recognition element comprising a boronate, arsenite or germanate group, or combinations thereof and X represents the number of recognition elements R bound to each chelator; X=0 to 4, and Y=1 to 4; and the number of recognition elements R may be the same or different, provided that for one or more chelators, X>0; and wherein the concentration of the analyte is detected by measuring any change in fluorescence emitted by the lanthanide metal chelate complex upon binding of the analyte to one or more chelators of the complex through the recognition element, wherein the ligand of the one or more chelators is an organic ligand comprising any one or more of a β-diketone or a nitrogen analog thereof, a cyclen, a dihydroxy, a carboxyl coordinating heterocycle, an enol, a macrobicyclic cryptand, a polyamino-polycarboxylic acid, a phenylphosphonic acid, an alkene group containing 1 to 10 carbon atoms, a heterocycle of nitrogen, sulfur or linked carboxyls, a phosphine oxide or a carbocyclic moiety, and wherein at least one ligand comprises, in addition to a member of the foregoing group, an aromatic group that does not directly chelate the lanthanide metal ion, said aromatic group being separated from said lanthanide metal ion by up to five atoms, and wherein the one or more chelators are anionic and contain a total of eight sites capable of coordination with the lanthanide metal ion.

2. The indicator molecule of claim 1, wherein M of the lanthanide metal chelate complex is an europium ion or a terbium ion.

3. The indicator molecule of claim 1, wherein the ligand of the one or more chelators comprises a moiety selected from the group consisting of a β-diketone and a cyclen.

4. The indicator molecule of claim 1, wherein the one or more chelators further comprises a substituent for attaching the chelate complex to a solid support.

5. The indicator molecule of claim 4, wherein the substituent for attaching the chelate complex to the solid support is a carboxyl, —NH₂ or —OH group.

6. The indicator molecule of claim 1, wherein the recognition element is selected from the group consisting of:

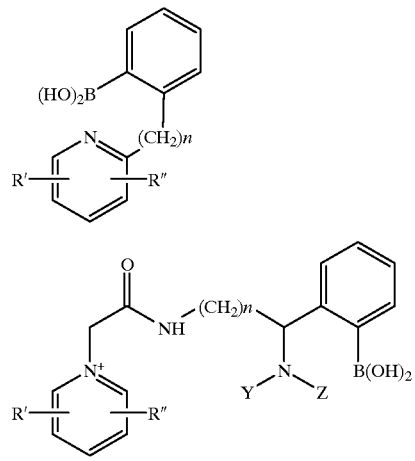

wherein n is 0, 1 or 2 in the right structure and 0 or 1 in the left structure;

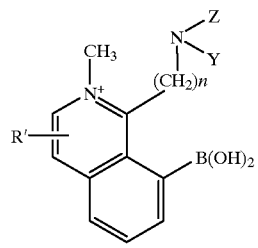

wherein n is 1;

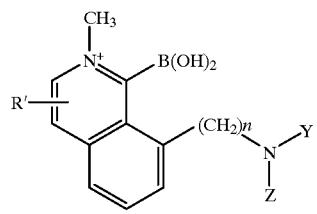

wherein n is 0 or 1;

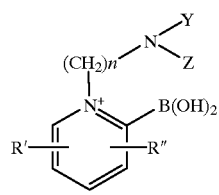

wherein n is 2;

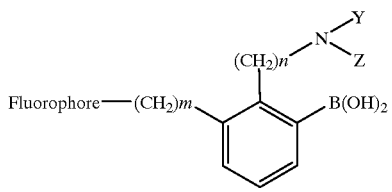

wherein m is 0–5 and n is 1 or 2; and

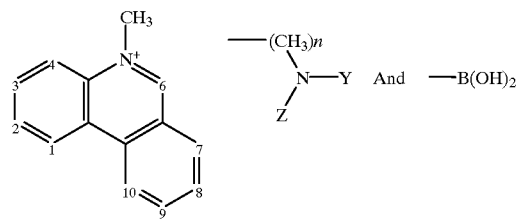

wherein n is 0 or 1, and the boronic acid and amine substituents are located as a pair on positions 1 and 10, 3 and 4, 6 and 7, 7 and 8 or 9 and 10;
and all structures, where applicable, R' and R" are each independently fused aryl; aliphatic; primary, secondary or tertiary amine; amide; carboxyl; ketone; ester; alcohol; or aldehyde; and Y and Z are each independently aliphatic, alkoxy or aryl; and derivatives thereof.

7. The indicator molecule of claim 1, wherein the boronate, arsenite or germanate group is attached to an aromatic moiety.

8. A fluorescent lanthanide metal chelate complex for detecting the concentration of an unlabeled analyte, having the formula:

$$M(-Ch(-R_x))_Y$$

wherein:
M is a lanthanide metal ion; Ch is a chelator comprising a ligand; R is an analyte-specific recognition element comprising a boronate, arsenite or germanate group, or combinations thereof and X represents the number of recognition elements R bound to each chelator; X=0 to 4, and Y=1 to 4; and the number of recognition elements R may be the same or different, provided that for one or more chelators, X>0; and wherein the concentration of the analyte is detected by measuring any change in fluorescence emitted by the lanthanide metal chelate complex upon binding of the analyte to one or more chelators of the complex through the analyte-specific recognition element, wherein the ligand of the one or more chelators is an organic ligand comprising any one or more of a β-diketone or a nitrogen analog thereof, a cyclen, a dihydroxy, a carboxyl coordinating heterocycle, an enol, a macrobicyclic cryptand, a polyamino-polycarboxylic acid, a phenylphosphonic acid, an alkene group containing 1 to 10 carbon atoms, a heterocycle of nitrogen, sulfur or linked carboxyls, a phosphine oxide or a carbocyclic moiety, and wherein at least one ligand comprises, in addition to a member of the foregoing group, an aromatic group that does not directly chelate the lanthanide metal ion, said aromatic group being separated from said lanthanide metal ion by up to five atoms, and wherein the one or more chelators are anionic and contain a total of eight sites capable of coordination with the lanthanide metal ion.

9. The fluorescent lanthanide metal chelate complex of claim 8, wherein M is an europium ion or a terbium ion.

10. The fluorescent lanthanide metal chelate complex of claim 8, wherein the ligand of the one or more chelators comprises a β-diketone or a cyclen.

11. The fluorescent lanthanide metal chelate complex of claim 8, wherein the recognition element is selected from the group consisting of:

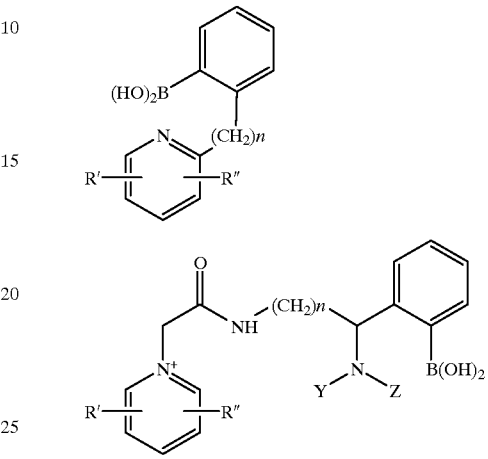

wherein n is 0, 1 or 2 in the right structure and 0 or 1 in the left structure;

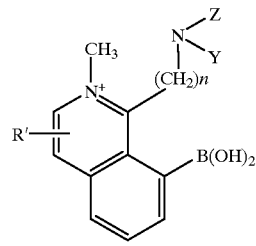

wherein n is 1;

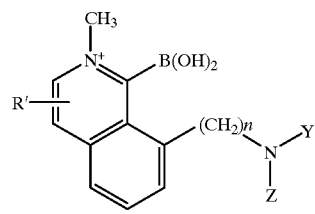

wherein n is 0 or 1;

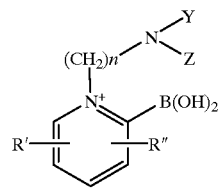

wherein n is 2;

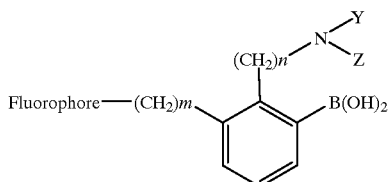

wherein m is 0–5 and n is 1 or 2; and

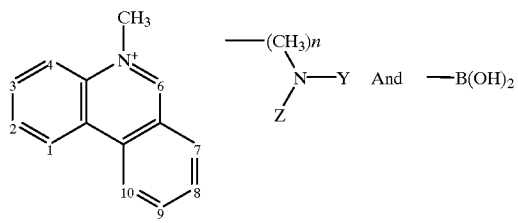

wherein n is 0 or 1, and the boronic acid and amine substituents are located as a pair on positions 1 and 10, 3 and 4, 6 and 7, 7 and 8 or 9 and 10;
and all structures, where applicable, R' and R" are each independently fused aryl; aliphatic; primary, secondary or tertiary amine; amide; carboxyl; ketone; ester; alcohol; or aldehyde; and Y and Z are each independently aliphatic, alkoxyr or aryl; and derivatives thereof.

12. The fluorescent lanthanide metal chelate complex of claim 8, wherein the boronate, arsenite or germanate group is attached to an aromatic moiety.

13. A method for detecting the concentration of an unlabeled analyte in a sample, comprising the steps of:
  a) exposing the sample to an indicator molecule comprising a fluorescent lanthanide metal chelate complex having the formula:

$$M(-Ch(-R_X))_Y$$

wherein:
M is a lanthanide metal ion; Ch is a chelator comprising a ligand; R is an analyte-specific recognition element comprising a boronate, arsenite or germanate group, or combinations thereof and X represents the number of recognition elements R bound to each chelator; X=0 to 4, and Y=1 to 4; and the number of recognition elements R may be the same or different, provided that for one or more chelators, X>0 wherein the ligand of the one or more chelators is an organic ligand comprising any one or more of a β-diketone or a nitrogen analog thereof, a cyclen, a dihydroxy, a carboxyl coordinating heterocycle, an enol, a macrobicyclic cryptand, a polyamino-polycarboxylic acid, a phenylphosphonic acid, an alkene group containing 1 to 10 carbon atoms, a heterocycle of nitrogen, sulfur or linked carboxyls, a phosphine oxide or a carbocyclic moiety, and wherein at least one ligand comprises, in addition to a member of the foregoing group, an aromatic group that does not directly chelate the lanthanide metal ion, said aromatic group being separated from said lanthanide metal ion by up to five atoms, and wherein the one or more chelators are anionic and contain a total of eight sites capable of coordination with the lanthanide metal ion; and
  b) measuring any change in fluorescence emitted by the lanthanide metal chelate complex upon binding of the analyte to one or more chelators of the complex through the analyte-specific recognition element, thereby detecting the concentration of the analyte.

14. The method of claim 13, wherein M of the lanthanide metal chelate complex is an europium ion or a terbium ion.

15. The method of claim 13, wherein the ligand of the one or more chelators comprises a β-diketone or a cyclen.

16. The method of claim 15, wherein the analyte is glucose.

17. The method of claim 13, wherein the recognition element is selected from the group consisting of:

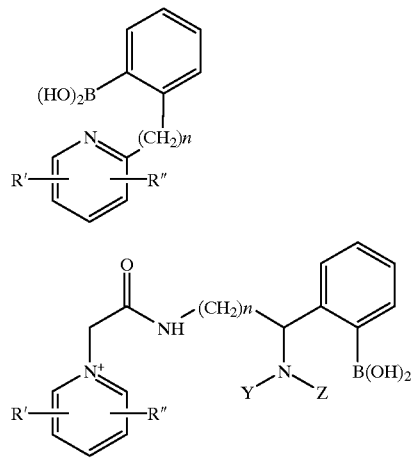

wherein n is 0, 1 or 2 in the right structure and 0 or 1 in the left structure

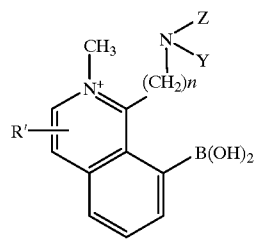

wherein n is 1;

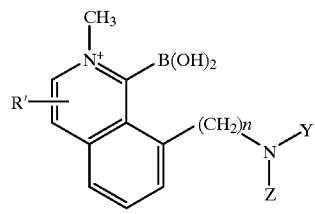

wherein n is 0 or 1;

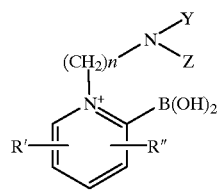

wherein n is 2;

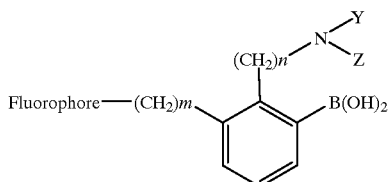

wherein m is 0–5 and n is 1 or 2; and

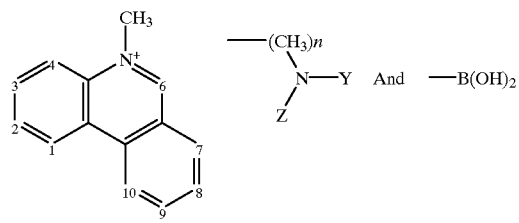

wherein n is 0 or 1, and the boronic acid and amine substituents are located as a pair on positions 1 and 10, 3 and 4, 6 and 7, 7 and 8 or 9 and 10;

and all structures, where applicable, R' and R" are each independently fused aryl; aliphatic; primary, secondary or tertiary amine; amide; carboxyl; ketone; ester; alcohol; or aldehyde; and Y and Z are each independently aliphatic, alkoxy or aryl;

and derivatives thereof.

18. The method of claim 13, wherein the boronate, arsenite or germanate group is attached to an aromatic moiety.

* * * * *